(12) United States Patent
Oldham et al.

(10) Patent No.: US 10,939,908 B2
(45) Date of Patent: *Mar. 9, 2021

(54) APPARATUS AND METHODS FOR LOADING A CLOSING DEVICE

(71) Applicant: Anchor Orthopedics XT Inc., Mississauga (CA)

(72) Inventors: Andrew Oldham, Georgetown (CA); Robert Harrison, Milton (CA); Neil Godara, Milton (CA); Ilinca Popovici, Toronto (CA)

(73) Assignee: Anchor Orthopedics XT, Inc., Mississauga (CA)

( * ) Notice: Subject to any disclaimer, the term of this patent is extended or adjusted under 35 U.S.C. 154(b) by 210 days.

This patent is subject to a terminal disclaimer.

(21) Appl. No.: 15/848,784

(22) Filed: Dec. 20, 2017

(65) Prior Publication Data
US 2018/0206840 A1    Jul. 26, 2018

Related U.S. Application Data

(60) Provisional application No. 62/438,158, filed on Dec. 22, 2016, provisional application No. 62/485,162, filed on Apr. 13, 2017.

(51) Int. Cl.
*A61B 17/06* (2006.01)
*A61B 17/04* (2006.01)
(Continued)

(52) U.S. Cl.
CPC .... *A61B 17/06114* (2013.01); *A61B 17/0401* (2013.01); *A61B 17/0469* (2013.01); *A61B 17/0487* (2013.01); *A61B 17/0491* (2013.01); *A61B 17/06004* (2013.01); *A61B 17/06061* (2013.01); *A61B 17/06066* (2013.01); *A61B 17/06128* (2013.01); *A61B 17/06133* (2013.01); *A61B 17/06166* (2013.01); *A61B 2017/0046* (2013.01); *A61B 2017/0053* (2013.01); *A61B 2017/00261* (2013.01);
(Continued)

(58) Field of Classification Search
CPC .......... A61B 17/0474; A61B 17/0469; A61B 17/0482; A61B 17/06004; A61B 17/0409; A61B 17/0477; A61B 2017/0496; A61B 2017/06052; A61B 17/0401; A61B 17/0483; A61B 17/0487; A61B 17/06
See application file for complete search history.

(56) References Cited

FOREIGN PATENT DOCUMENTS

WO    WO 2014/141208    *    8/2014

* cited by examiner

*Primary Examiner* — Katherine M Shi
(74) *Attorney, Agent, or Firm* — Vincent Man; Glenn Arnold; Samuel Tekie

(57) ABSTRACT

A method and apparatus are disclosed for loading a closing device onto a delivery device at the point of use and for using the apparatus for treating the intervertebral disc. The apparatus includes a cartridge for loading a closing device onto a delivery device at the point of use, the cartridge comprising a tab holding feature for holding one or more tabs of the closing device and a tab loading feature for loading tabs onto the delivery device. A method of treating an intervertebral disc includes the steps of loading a closing device into a delivery device at the point of use, the closing device comprising at least two tabs coupled to a connecting element, and substantially approximating a defect in the intervertebral disc using the closing device delivered by the delivery device.

4 Claims, 31 Drawing Sheets

(51) Int. Cl.
    *A61B 17/00*       (2006.01)
    *A61B 17/08*       (2006.01)
    *A61B 90/00*       (2016.01)

(52) U.S. Cl.
    CPC ................ *A61B 2017/0409* (2013.01); *A61B 2017/0417* (2013.01); *A61B 2017/0464* (2013.01); *A61B 2017/0474* (2013.01); *A61B 2017/0496* (2013.01); *A61B 2017/06052* (2013.01); *A61B 2017/06142* (2013.01); *A61B 2017/06157* (2013.01); *A61B 2017/081* (2013.01); *A61B 2090/034* (2016.02)

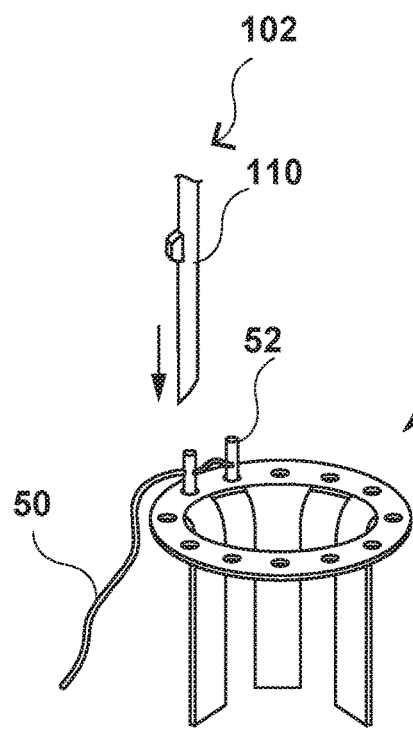
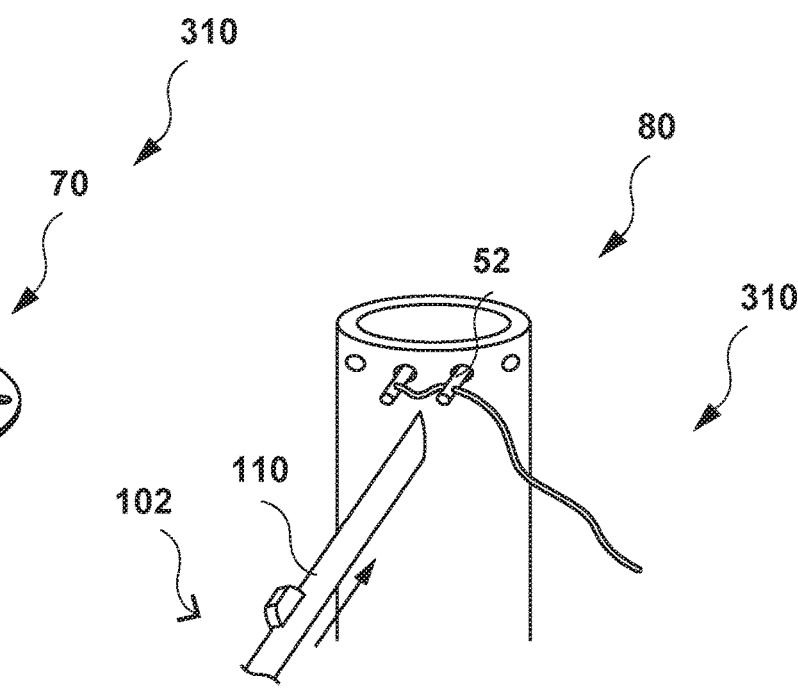
FIG.1G  FIG. 1H
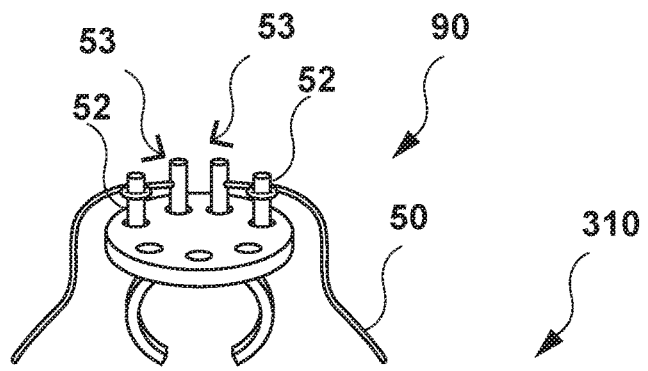
FIG.1I

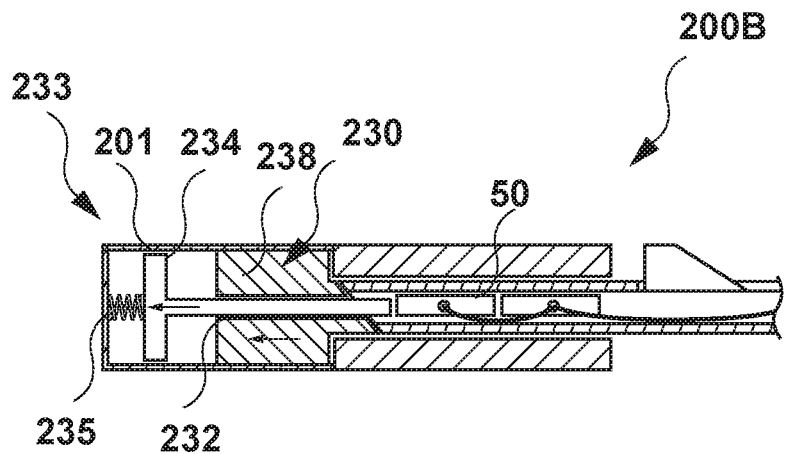
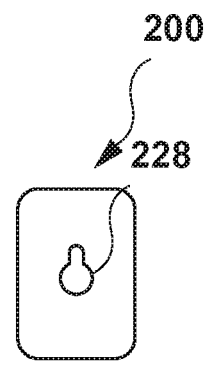
FIG. 2A  FIG. 2B
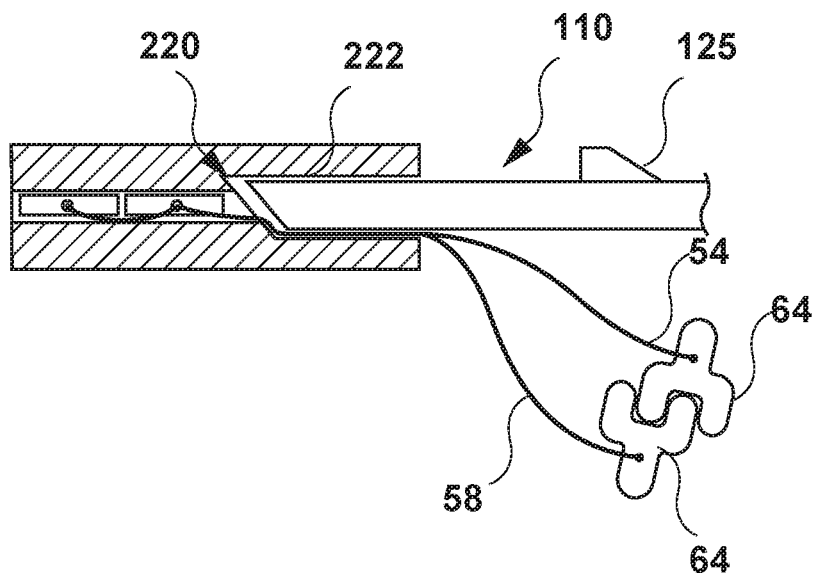
FIG. 2C

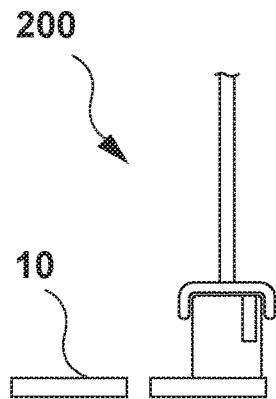
FIG. 2F
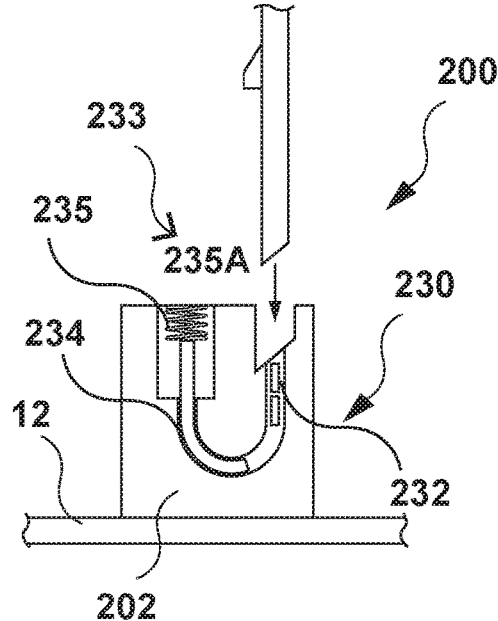
FIG. 2G
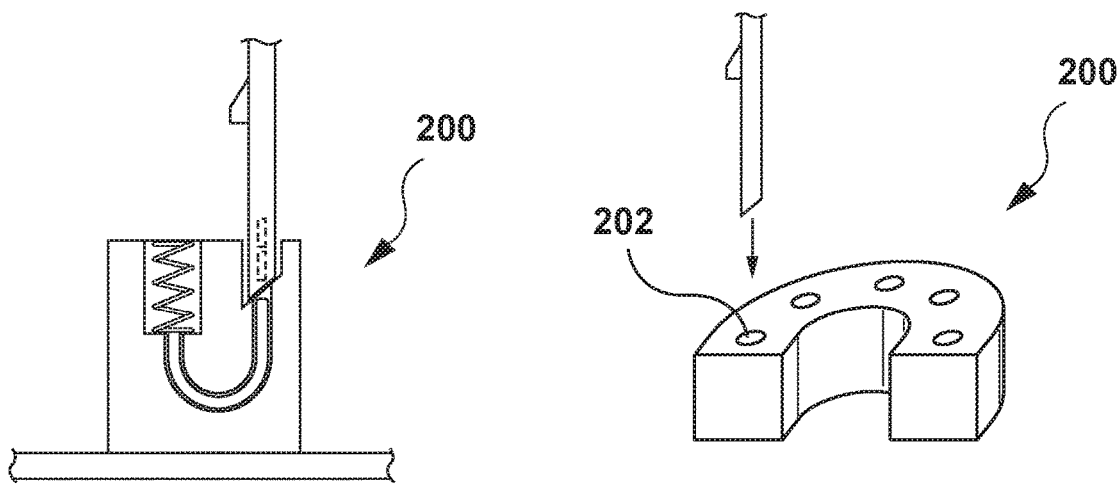
FIG. 2H
FIG. 2I

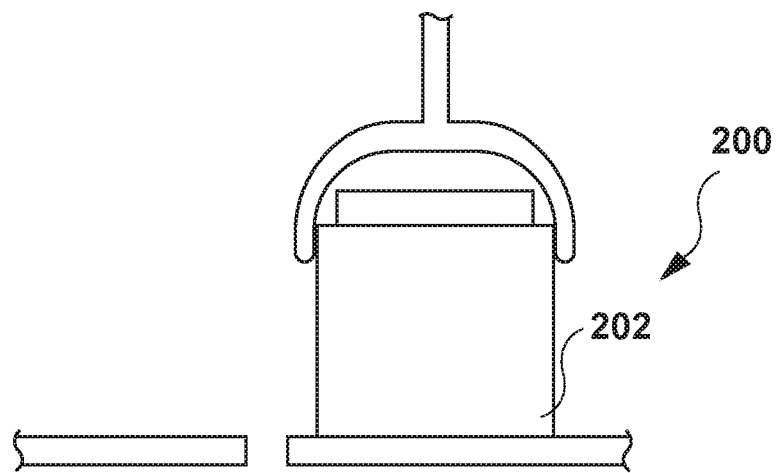
FIG. 3E
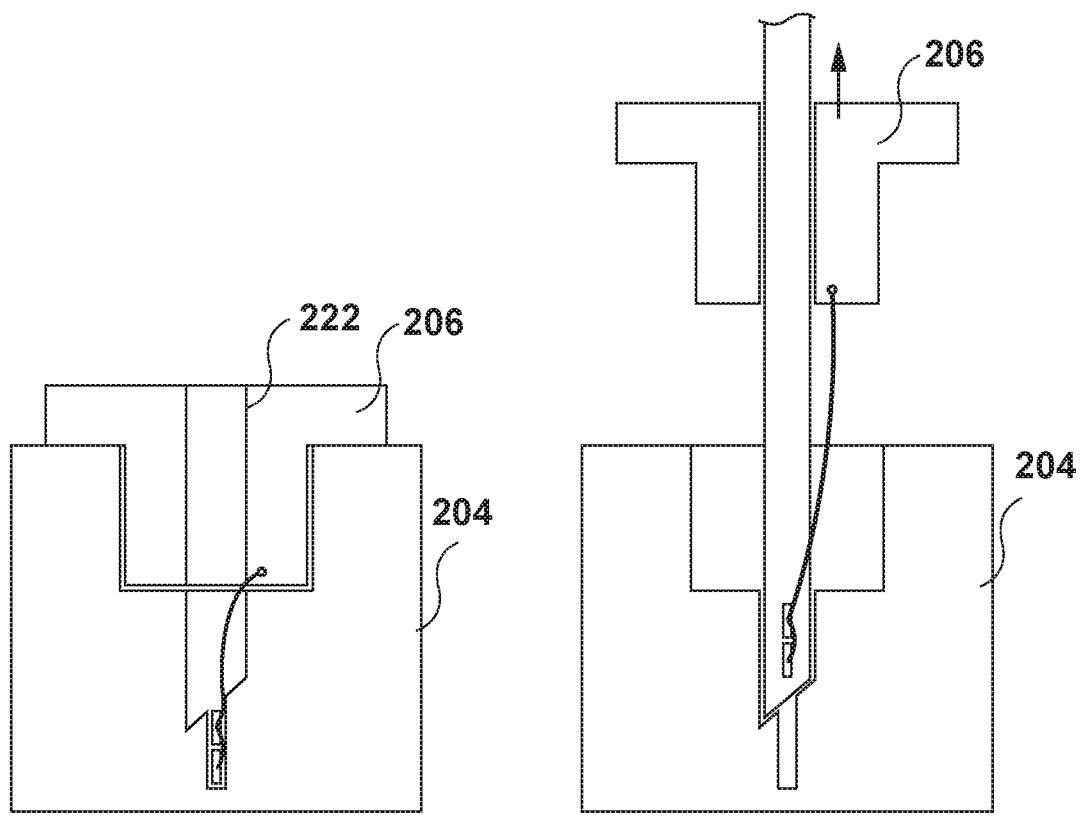
FIG. 3F
FIG. 3G

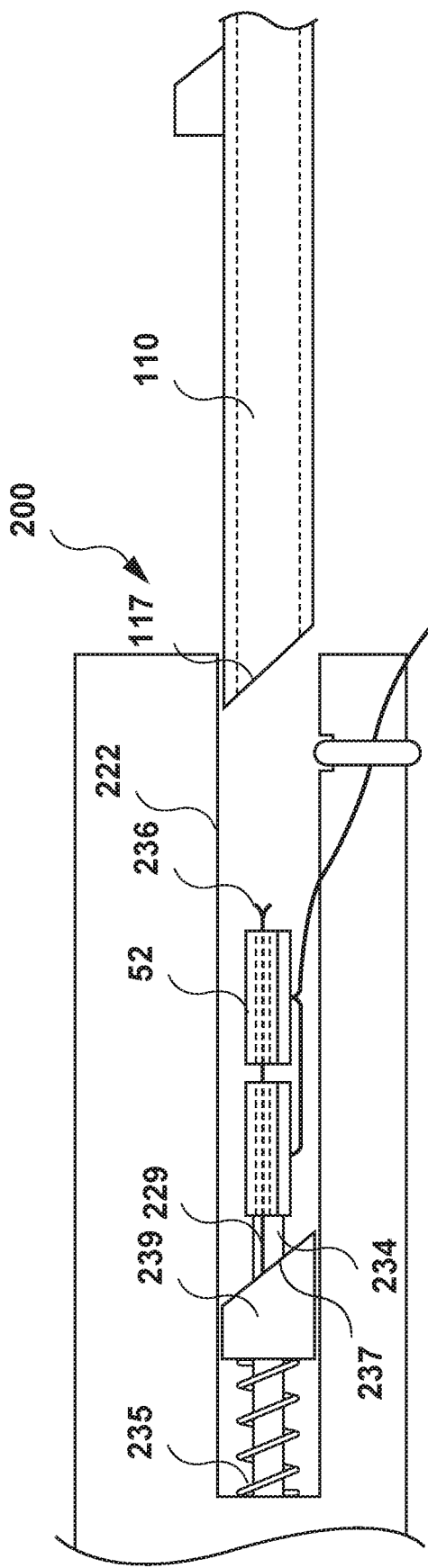
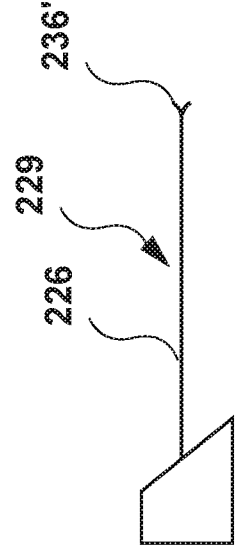
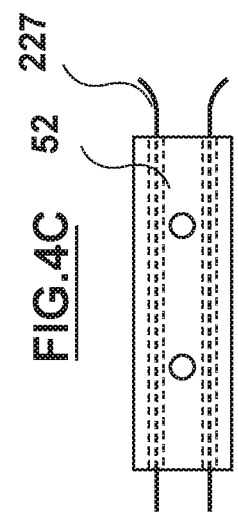
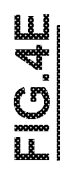
FIG. 4A
FIG. 4B
FIG. 4C
FIG. 4D
FIG. 4E

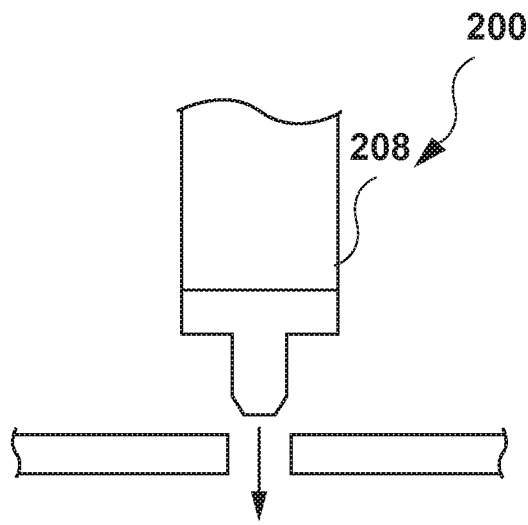
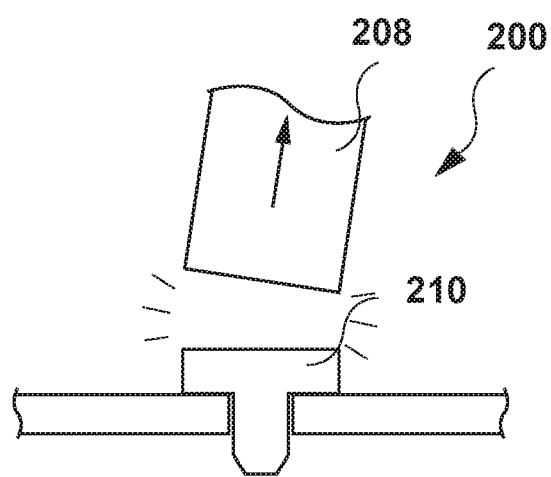
FIG.4F
FIG. 4G
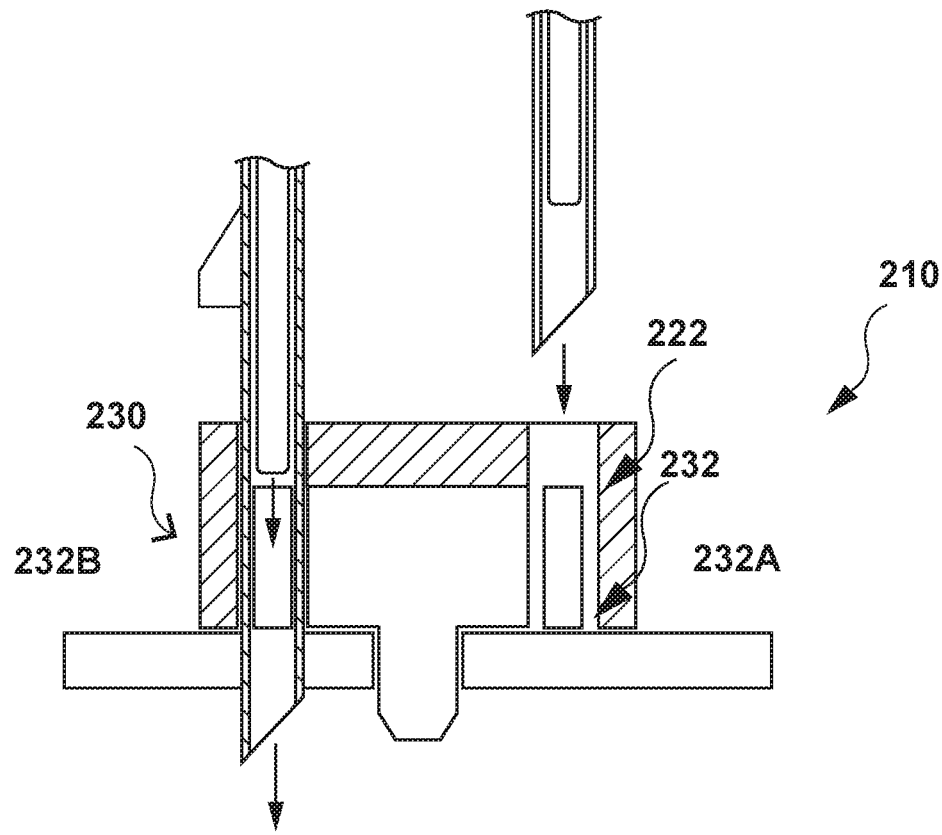
FIG. 4H

FIG.K4

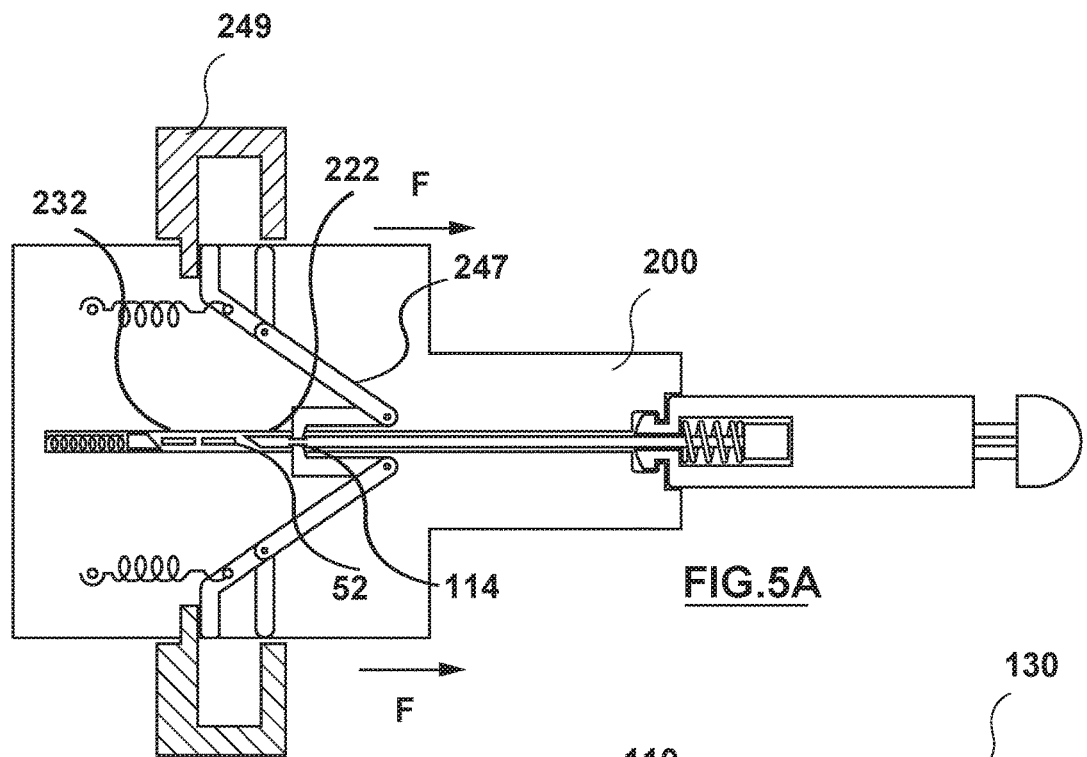
FIG.5A
FIG.5B
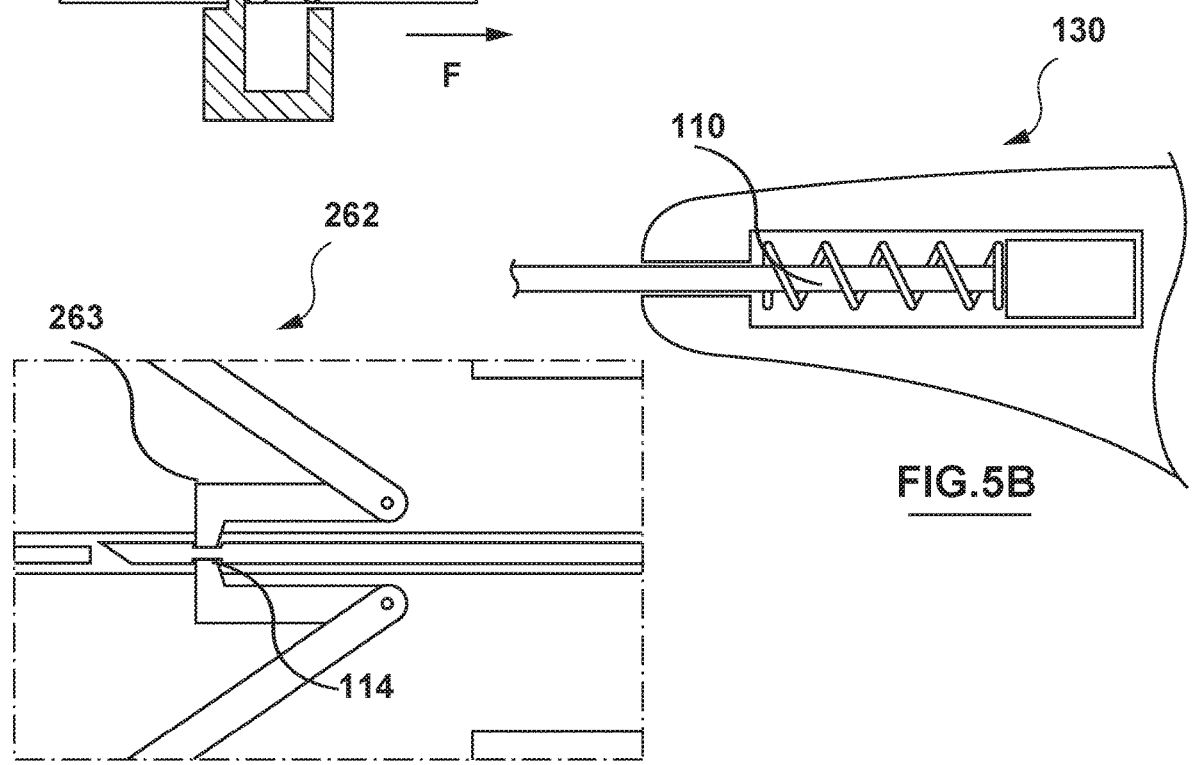
FIG.5C

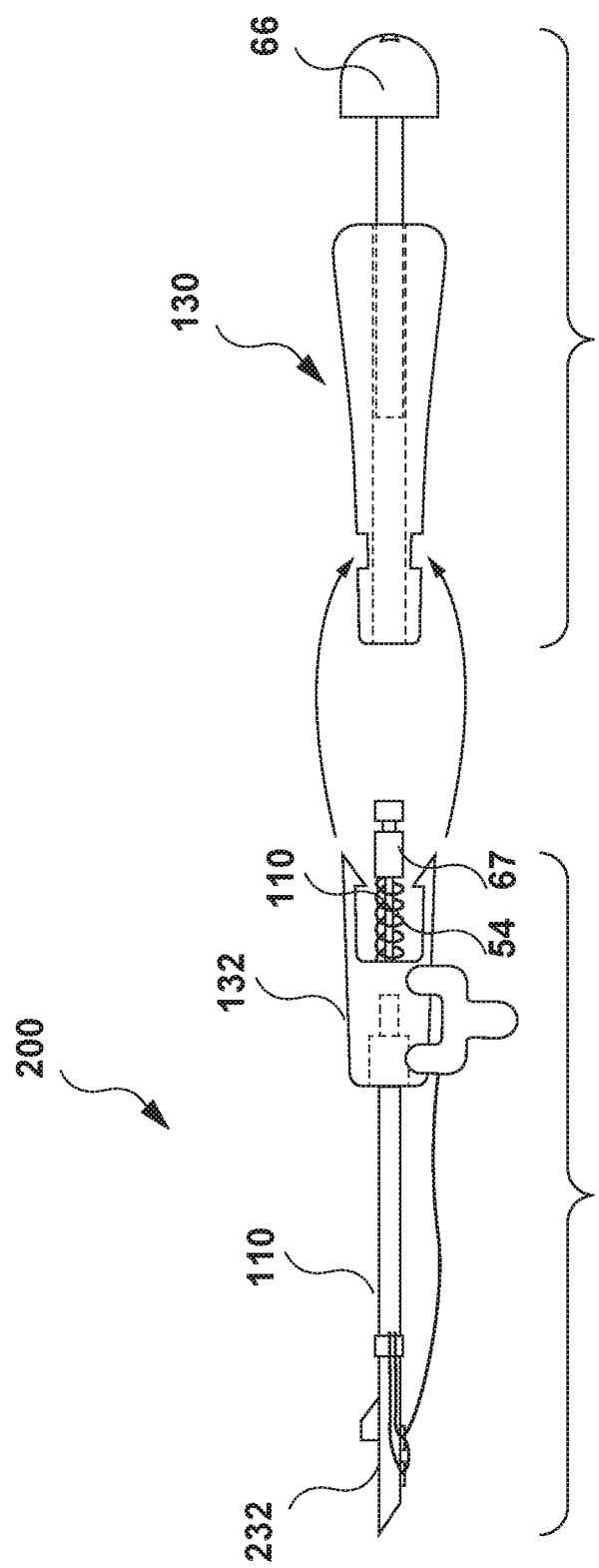

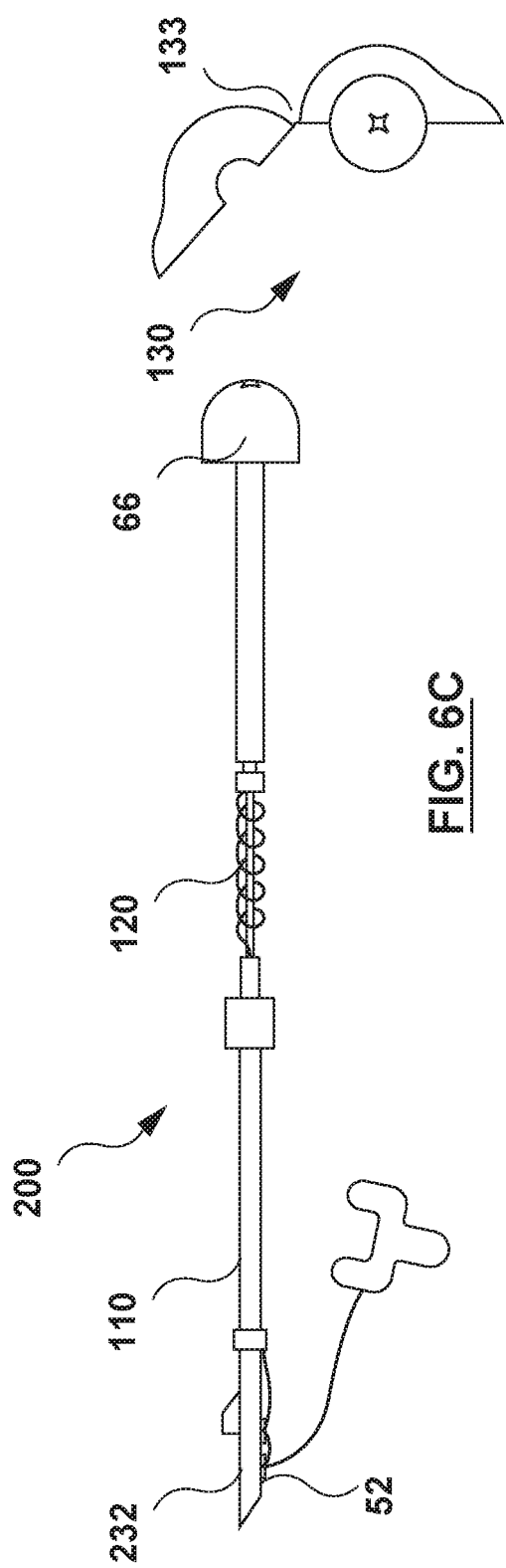
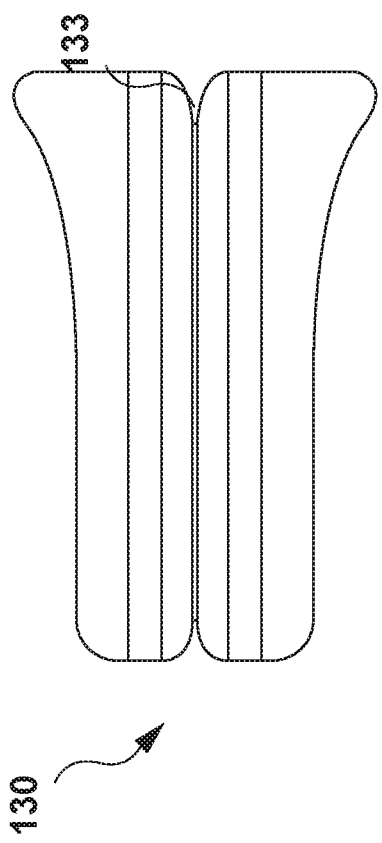
FIG. 6C
FIG. 6D
FIG. 6E

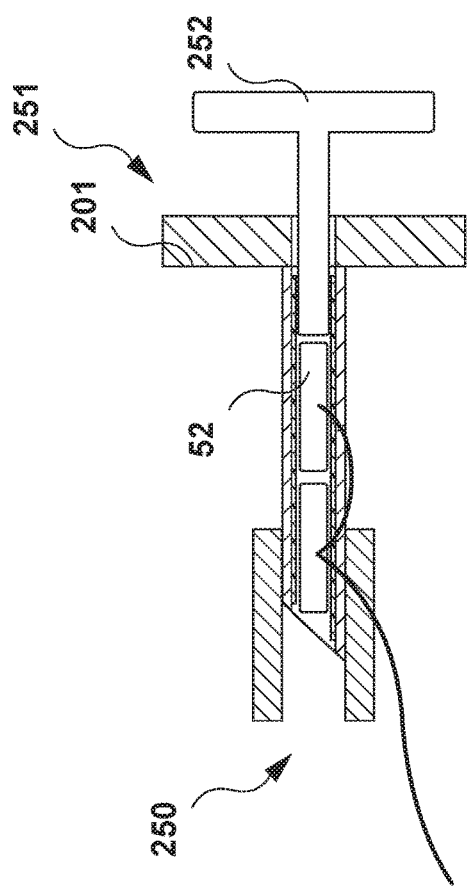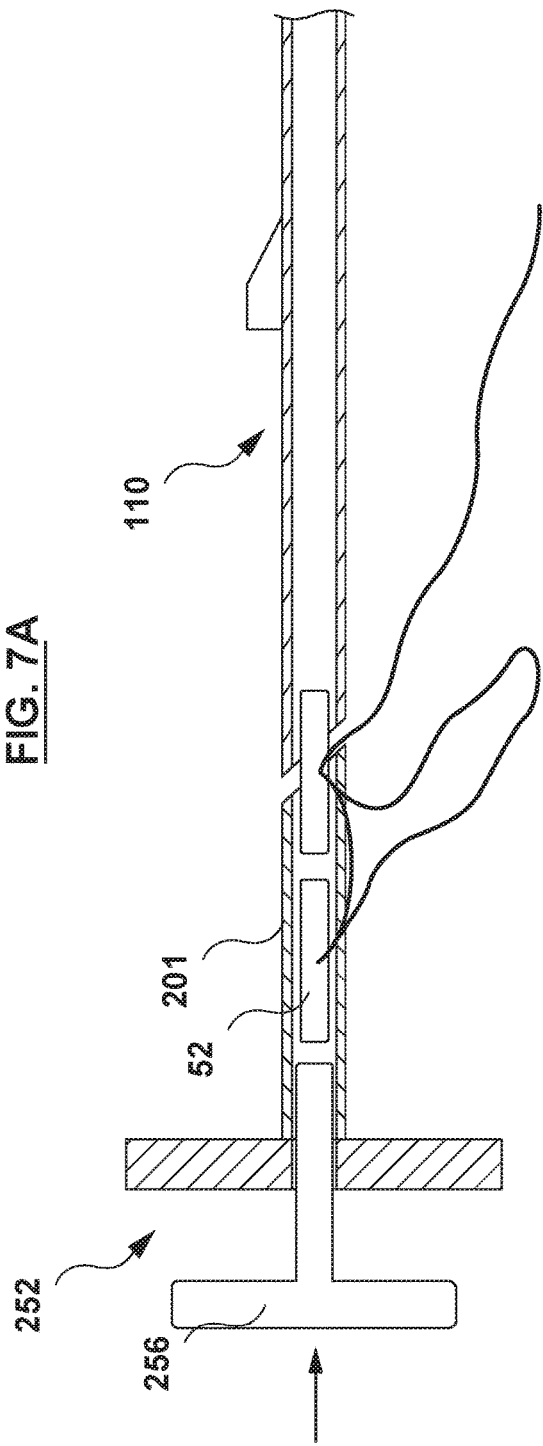

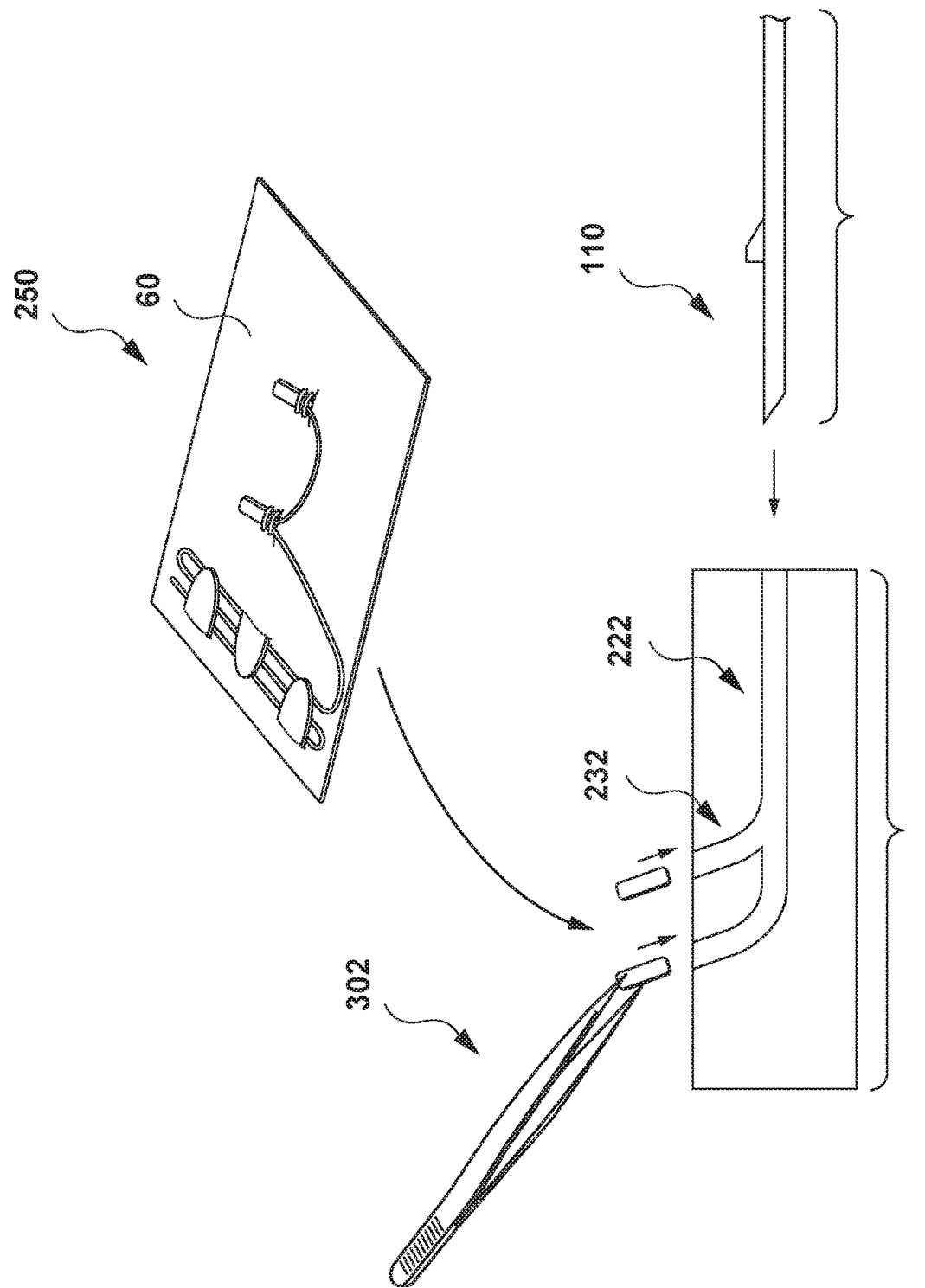

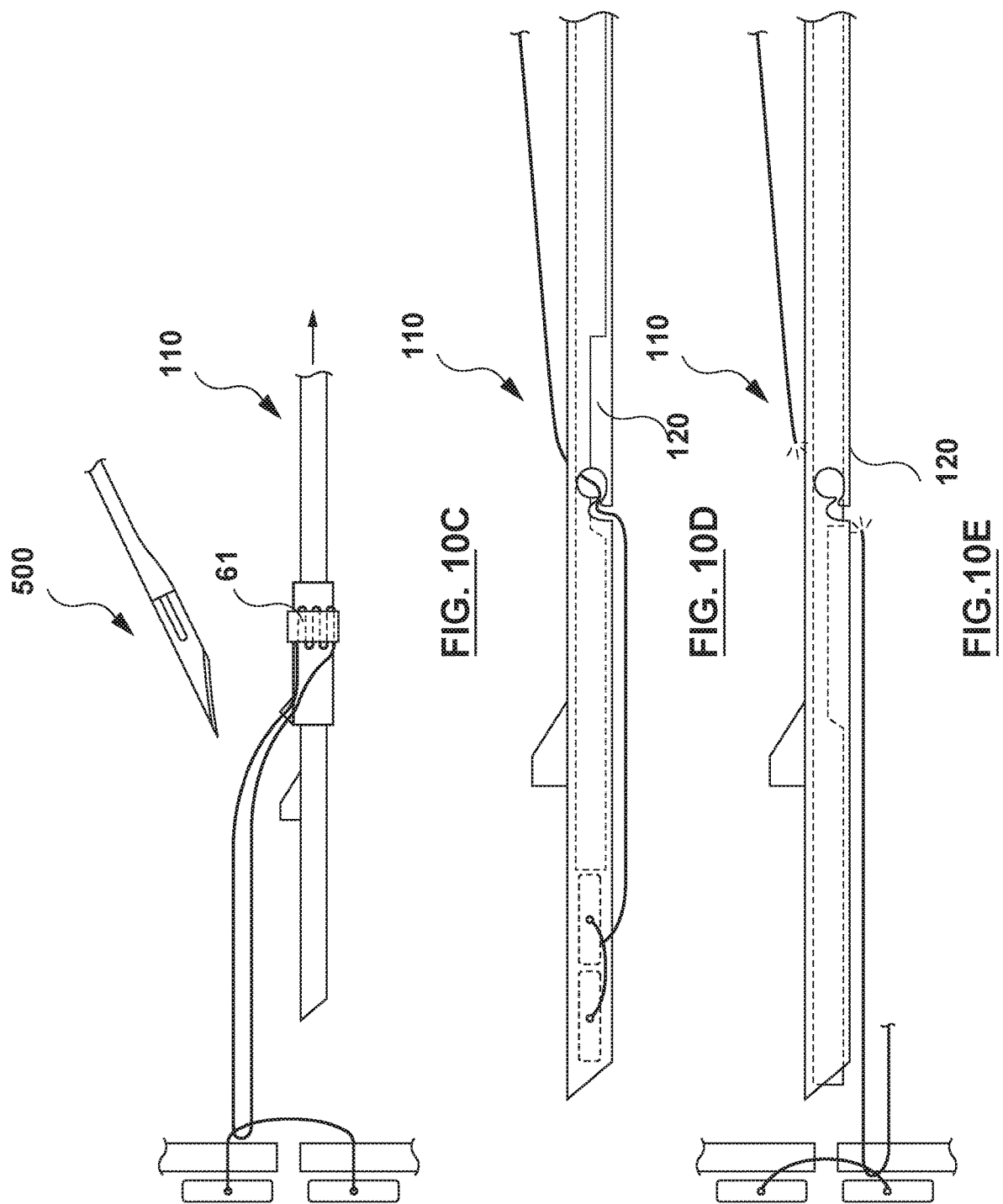

APPARATUS AND METHODS FOR LOADING A CLOSING DEVICE

CROSS-REFERENCE TO RELATED APPLICATIONS

This application claims the benefit of U.S. Provisional Patent Application Ser. No. 62/438,158, filed on Dec. 22, 2016, and U.S. Provisional Patent Application Ser. No. 62/485,162, filed on Apr. 13, 2017. Both of the aforementioned Provisional patent applications are hereby incorporated herein by reference in their entirety.

TECHNICAL FIELD

The disclosure relates to a loading device for loading a surgical instrument. More specifically, the disclosure relates to device and methods for loading an implement such as a closing device onto a delivery device.

BRIEF DESCRIPTION OF THE DRAWINGS

In order that the invention may be readily understood, embodiments of the invention are illustrated by way of examples in the accompanying drawings, in which:

FIGS. 1B-1I are illustrations of a loading device in accordance with an embodiment of the present invention using a passive loading mechanism;

FIGS. 2A-2B are illustrations of a loading device in accordance with an embodiment of the present invention using a push mechanism;

FIG. 2C is an illustration of a loading device in accordance with an embodiment of the present invention using a pull mechanism;

FIGS. 2D-2I are illustrations of a loading device in accordance with an embodiment of the present invention using a push mechanism;

FIGS. 3A-3G are illustrations of a loading device in accordance with an embodiment of the present invention using a pull mechanism;

FIGS. 4A-4E are illustrations of a loading device in accordance with an embodiment of the present invention using an eat-push mechanism;

FIGS. 4F-4L are illustrations of alternate loading devices in accordance with various embodiments of the present invention;

FIGS. 5A-5C are illustrations of a loading device in accordance with an alternate embodiment of the present invention using an eat pull mechanism;

FIGS. 6A-6J are illustrations of loading devices in accordance with alternate embodiments of the present invention;

FIGS. 7A-7F are illustrations of loading devices in accordance with alternate embodiments of the present invention;

FIGS. 9A-9C are illustrations of loading devices in accordance with alternate embodiments of the present invention;

FIGS. 10A-10E are illustrations of loading devices in accordance with alternate embodiments of the present invention.

DETAILED DESCRIPTION

Figure 1A:
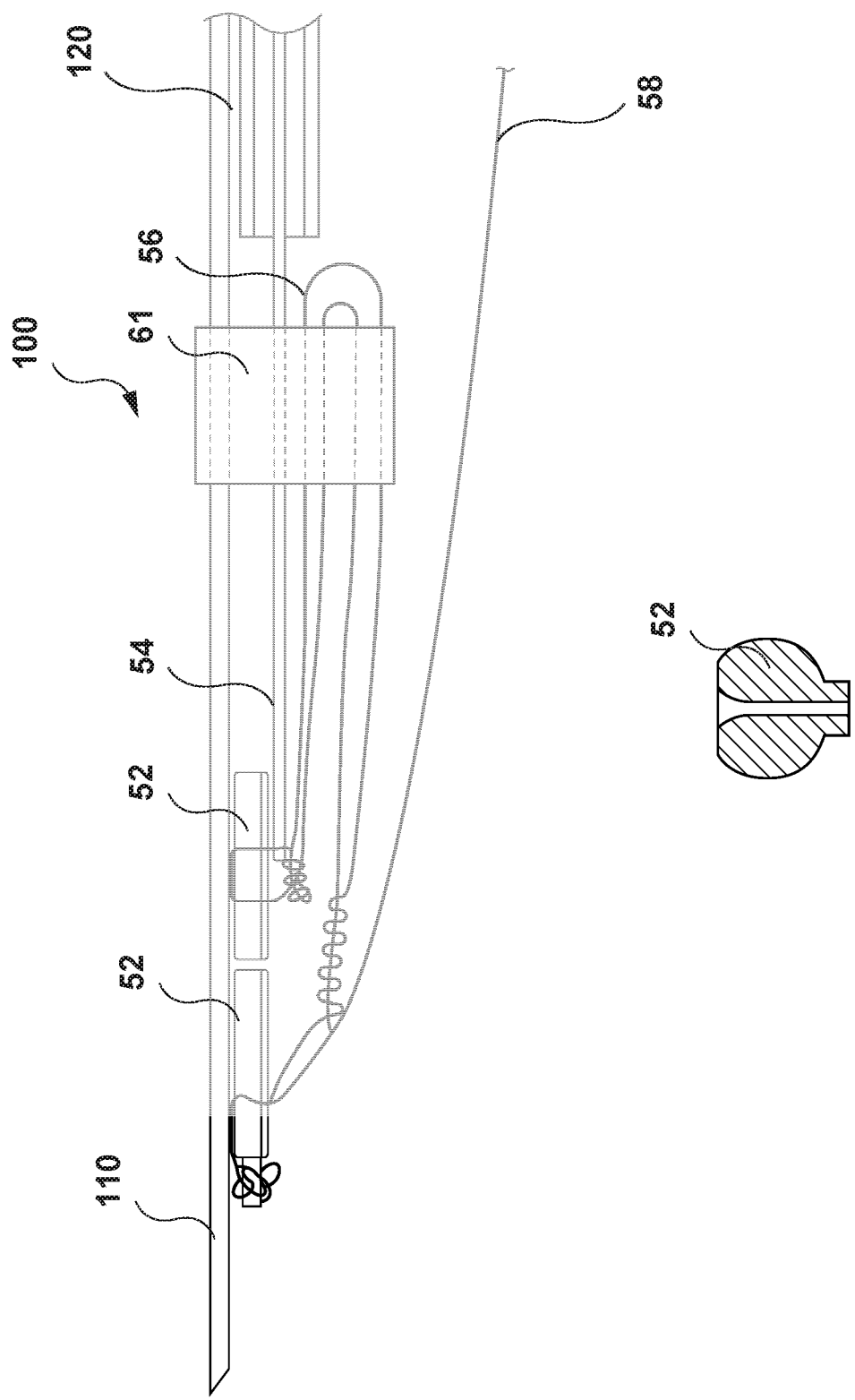
FIG. 1A is an illustration of a delivery device that is usable with a loading device in accordance with an embodiment of the present invention.

A delivery device may be used to deliver an implement or closing device into a targeted site within a patient's body for example to treat the tissue site. Such delivery devices may be especially useful for delivering an implement deep into the patient's body where access may be limited. For example, some delivery devices may be used to deliver a closing device into the patient's body where access is provided to the tissue through a portal. In some such embodiments, the tissue to be treated may be located in a sensitive region of a patient's body, where it is advantageous to complete the procedure in a timely and efficient manner while minimizing undue risk to the patient. For example, the procedure may be for performing herniated disc repair. Furthermore, there may be limited visibility and access when accessing the site through a portal. As such, limited information may be available to the user regarding the positioning of the implement within the delivery device prior to use. For example, limited information may be available to confirm whether the implement has been properly loaded into the delivery device and is adequately positioned for delivery. As such there is a need in the art to provide a means to reliably and efficiently load a closing device such as suture into a delivery device.

In some such situations, certain challenges may be faced when preparing the delivery device for delivering the implement or object into the patient's body. More specifically, it may be difficult to load an implement such as a suture or tab into the delivery device. In some situations attempting to load the implement into the delivery device may be too cumbersome and time consuming and may cause unnecessary procedural delay.

As such, inventors of the present invention have developed a novel means for loading an implement into a delivery device.

In one broad aspect, some embodiments of the present invention provide methods and devices for facilitating loading of an implement such as a closing device onto a delivery device at the point of use. As a feature of this broad aspect, some embodiments of the present invention provide methods and devices for putting an implement such as a closing device onto the delivery device at the point of use to perform herniated disc repair.

In one broad aspect, embodiments of the present invention provide a method for loading an implement onto a delivery device at the point of use.

In a further broad aspect, embodiments of the present invention provide a loading device for loading an implement onto a delivery device.

In still a further broad aspect, embodiments of the present invention provide a loading device for loading an implement onto a delivery device, wherein the loading device may remain coupled to the delivery device for the remainder of the procedure.

In still a further broad aspect, embodiments of the present invention provide at least two loading devices for loading an implement onto a delivery device. As a feature of this broad aspect, the at least two loading devices are used substantially concurrently to load the implement onto the delivery device. As another feature of this broad aspect, the at least two loading devices are used sequentially to load the implement onto the delivery device. As still another feature of this broad aspect, the at least two loading devices comprise three or more loading devices for loading an implement onto the delivery device.

In one broad aspect, embodiments of the present invention provide a method of treating an intervertebral disc, the method comprising: loading a closing device into a delivery device at the point of use, the closing device comprising at least two tabs coupled to a connecting element; and substantially approximating a defect in the intervertebral disc using the closing device delivered by the delivery device.

In another broad aspect, embodiments of the present invention provide a cartridge for loading a closing device onto a delivery device at the point of use, the cartridge comprising: a tab holding feature for holding one or more tabs of the closing device; and a tab loading feature for loading tabs onto the delivery device. The tab loading feature may also be understood to be transferring one or more tabs onto the delivery device and, therefore, the term "loading/transferring" may be used in this specification to refer to the functionality of this component.

As a feature of this broad aspect, the cartridge comprises a tether holding feature for holding a tether of the closing device; and a tether loading/transferring feature for loading the tether onto the delivery device.

As another feature of this broad aspect, the cartridge further comprising: a suture holding feature for holding a suture coupled to the one or more tabs, wherein each of the tabs is coupled to an end of the suture; and a suture loading/transferring feature for loading the suture onto the delivery device for securing the suture thereto.

As still another feature of this broad aspect, the cartridge further comprises a delivery device engagement feature for co-operatively engaging with the delivery device to enable transfer of the one or more tabs onto the delivery device. This feature may also assist in alignment of the cartridge (or a portion thereof) with the delivery device and may therefore be referred to an "engagement/alignment" feature.

As still another feature of this broad aspect, the cartridge comprises a tab holding feature comprises a seat for holding the one or more tabs therein; and the delivery device engagement feature comprises a delivery device receiving passage in communication with the seat for receiving a portion of the delivery device therein.

As another feature of this broad aspect, the delivery device engagement/alignment feature comprises a needle engagement/alignment feature for co-operatively engaging with the delivery device to enable transfer of the one or more tabs into a needle of the delivery device.

As another feature of this broad aspect, the tab holding feature comprises a tab holding passage defining a seat for holding the one or more tabs therein; and the needle engagement feature comprises a needle receiving passage in communication with the tab holding passage for receiving the needle therein.

As a further feature of this broad aspect, the seat defines a tab holding passage for holding the one or more tabs.

As a further feature of this broad aspect, the seat defines a projection for holding the one or more tabs thereon.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In one broad aspect, embodiments of the present invention comprise one or more devices and methods for loading an implement onto a delivery device at the point of use.

In a specific example, as shown in FIG. 1A, a delivery device 100 is shown that is used to treat a defect within a region of tissue. The delivery device 100 is used to deliver an implement or closing device 180, as additionally shown in FIG. 1B. The closing device or implement 180 comprises a connecting member, such as a suture 50, as well as tabs 52 affixed to each end of the connecting member. In a particular example, tabs 52 may comprise PEEK injection molded tabs. Although the term "suture" is used throughout this description, it should be understood that other connecting members may be used.

More specifically, referring again to FIG. 1A, the delivery device 100 comprises a suture passer that comprises a needle 110 and a stylet 120 that is positioned within the lumen of the needle 110 and extends at least partially there-through. The tabs 52 and the suture 50 reside inside the end of the needle 110 of the suture passer 102 and are fixed in place by a tether 54 that extends through the lumen of the stylet 120. In some examples, the tether 54 along with the tabs 52 forms a tab assembly. In some examples, the extra suture such as the service loop 56 and the locker strand 58 are managed external to the suture passer 102 using an affixing means 65. For example, the service loop 56 is coupled to the needle 110 using an affixing means comprising an elastic band or a suture retention band 61 coupled to the needle 110. In one example, the locker strand 58 is coupled to the suture passer 102 using an affixing means 65 comprising a clip 64 that attached to a handle 130 of the suture passer 102. [Shown later in FIG. 2C]

In accordance with some embodiments of the present invention, one more devices and methods are disclosed for loading the implement or closing device 180 into the suture passer 102. In some such examples, some embodiments of methods and devices of the present invention may provide a loading device or a cartridge 200 comprising one or more of: (i) a means for loading the tabs 52 into the suture passer 102, (ii) a means of loading the tether 54 into the suture passer 102, and (iii) a means for loading the suture 50 (which includes the service loop 56 and the locker strand 58) into the suture passer 102.

In some embodiments of a cartridge of the present invention, a loading device or cartridge 200 is provided for loading the implement or closing device 180 onto the suture passer 102. The cartridge comprises a tab holding/transfer feature. In some such embodiments, the cartridge 200 may comprises a tab holding feature 231 for holding one or more tabs of the closing device, and a tab loading/transferring feature 233 for loading tabs onto the delivery device. The cartridge 200 may additionally comprise tether holding/transfer features. Specifically, the cartridge 200 may comprise a tether holding feature 241 for holding a tether of the closing device and a tether loading/transferring feature 243 for loading the tether onto the delivery device. The cartridge 200 may additionally comprise suture holding/transfer features. Specifically, the cartridge may additionally comprise a suture holding feature 251 for holding a suture coupled to the one or more tabs, wherein each of the tabs is coupled to an end of the suture. The cartridge may comprises a suture loading/transferring feature 253 for loading the suture onto the delivery device for securing the suture thereto.

Passive Loading Devices/Basic Style Loading Devices

In some embodiments of the present invention a loading device or a cartridge 200 is provided to load an implement such as closing device onto the delivery device such as a suture passer 102. In one such example, the loading device or cartridge 200 comprises a passive means or mechanism for loading the closing device 180 onto the delivery device such as the suture passer 102. In one such example, a manual or passive means is provided to load the closing device from the loading device or cartridge 200 onto the delivery device such as the suture passer.

Direct Mechanism

In some such examples, a direct means is provided for loading the closing device 180 onto the suture passer 102. In other words, the closing device 180 is loaded directly onto the suture passer 102 without requiring the use of, or without actually using, an additional device.

Figure 1B:
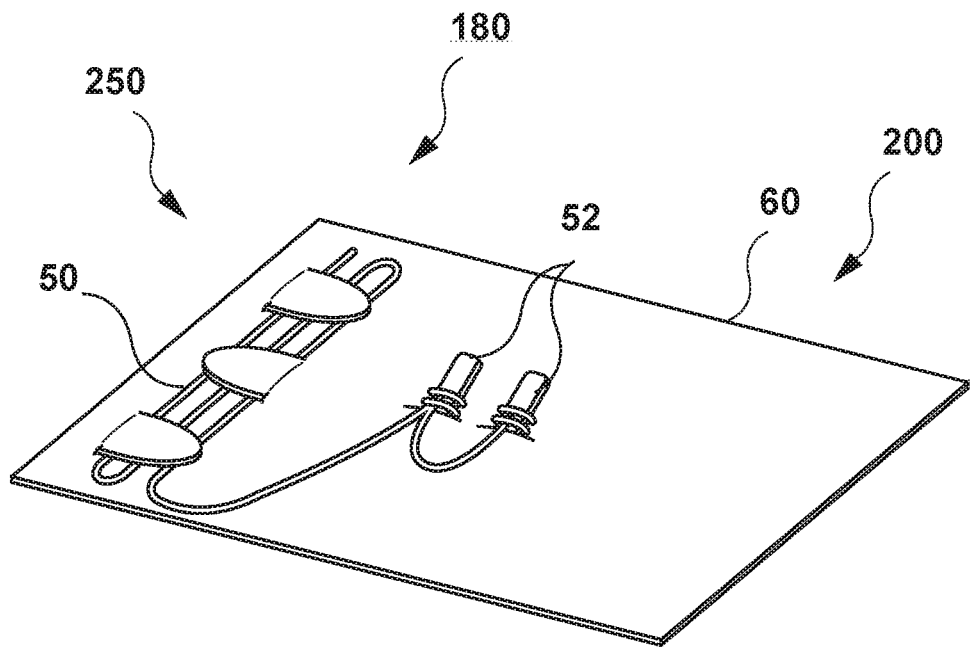

In accordance with one embodiment of the present invention, [as shown in FIG. 1B], a loading device or cartridge 200 is provided that utilizes a passive mechanism for loading the closing device 180 onto the delivery device 100. In one such example, the loading device or cartridge 200 comprises a die card 60 and the implement or closing device 180 is provided on the die card 60. In other words, the loading device or cartridge 200 defines a tab holding feature 231 for holding the tabs 52 and a suture holding feature 251 for holding the suture therein. In some such embodiments a method is provided where the method comprises using the suture passer to grab tabs 52, such as pair of tabs 53 from the die card 60. In some such examples, the die card 60 may additionally provide a tether holding feature.

Figures 1C, 1D:
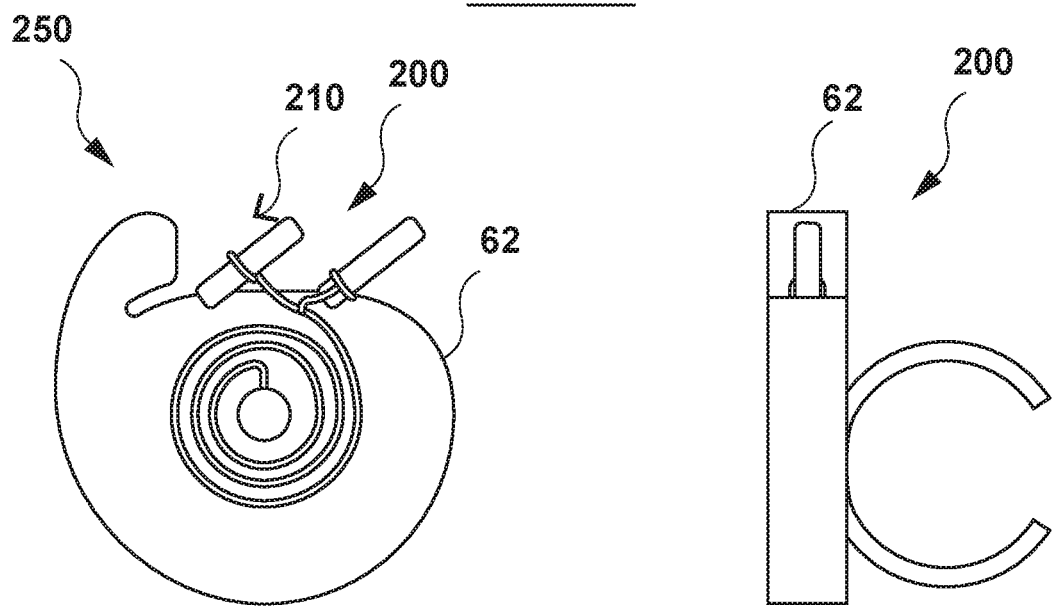
Figure 1E:
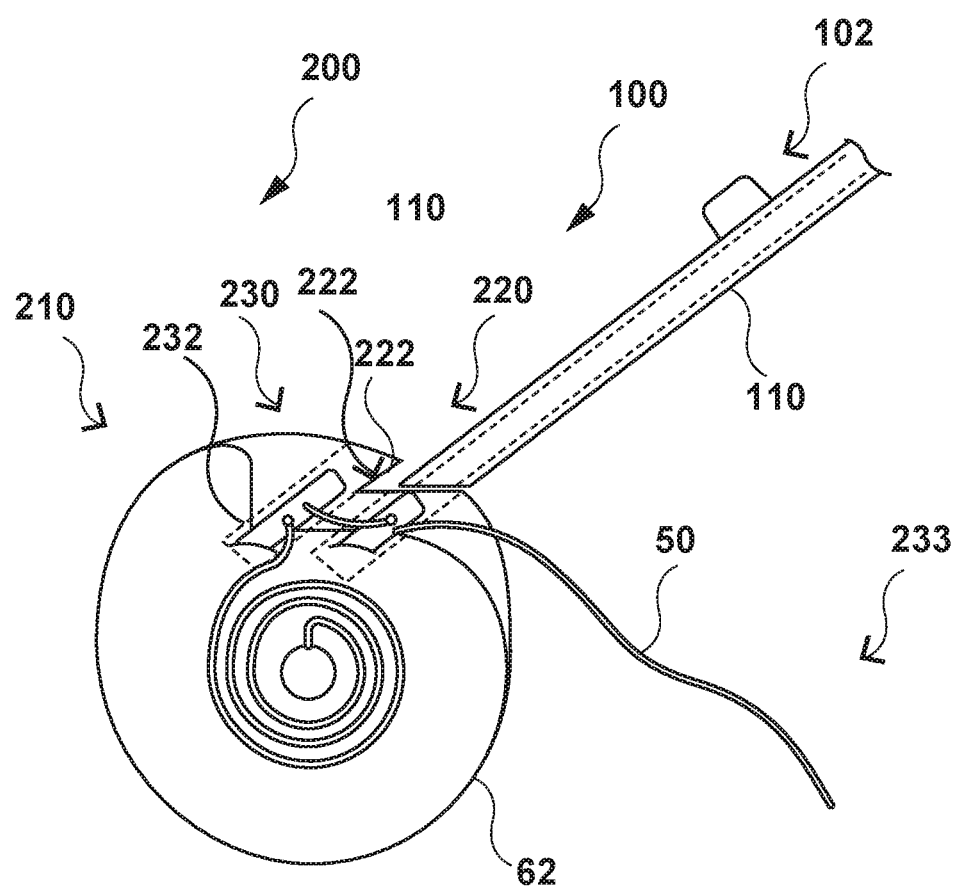

Alternatively, the implement or closing device 180 may be provided on a cartridge 200 comprising ligating reel or a suture spool 62 as shown in FIGS. 1C and 1D. The cartridge comprises a tab holding feature 231 for holding the tabs therein. In one such example, as additionally shown in FIG. 1E, the tab holding feature 231 comprises a seat 230 for holding the one or more tabs 52, such as a pair of tabs 53 therein. In some such examples, the method comprises using the suture passer 102 to grab the tabs 52 from the ligating reel 62, In one such example, [as shown in FIG. 1E], the method comprises steps of advancing the needle 110 to mate with the ligating reel or suture spool 62 may be provided with a pull string which may be formed from the suture 50, which may be pulled to assist with loading of the tabs 52, such as the pair of tabs 53, into the needle 110 of the suture passer 102. In one such example, the tab transferring feature 233 is defined by the pull string formed by the suture 50.

In one such example, as additionally shown in FIG. 1E, the cartridge further comprises a delivery device engagement/alignment feature 220 for co-operatively engaging with the delivery device to enable transfer of the one or more tabs onto the delivery device. More specifically, the seat 230 defines the tab holding feature 231 comprising a tab holding passage 232 for holding the pair of tabs 53 therein. The delivery device engagement/alignment feature 220 comprises a delivery device receiving passage 222 (such as a needle receiving passage) in communication with the tab holding passage 232 for receiving a portion of the delivery device 100 therein. In one such example, as shown in FIG. 1E, the delivery device 100 comprises the suture passer 102, as described herein above. In one such example, the delivery device alignment feature 220 comprises a needle engagement or alignment feature for co-operatively engaging with the needle 110 of suture passer 102 to enable transfer of the one or more tabs into the needle 110. The needle engagement feature comprises a needle receiving passage in communication with the tab holding passage 232 for receiving the needle 110 therein.

In accordance with a method of the present invention, a method is provided for treating an intervertebral disc the method comprises: loading a closing device 180 into a delivery device at the point of use using a cartridge 200, the closing device 180 comprising tabs 52 attached to a suture and using the delivery device 100 to substantially approximate a defect of the intervertebral disc by means of the closing device 180. The term "close" or "closed" and variations thereof are used herein to refer to an approximation of the tissue surrounding or defining the defect in the tissue, which may result in complete or partial closure of the defect.

Indirect Mechanism

In accordance with some embodiments of the present invention, an indirect means is provided for loading the closing device 180 onto the suture passer 102. In other words, the closing device 180 is loaded indirectly onto the suture passer 102.

Figure 1F:
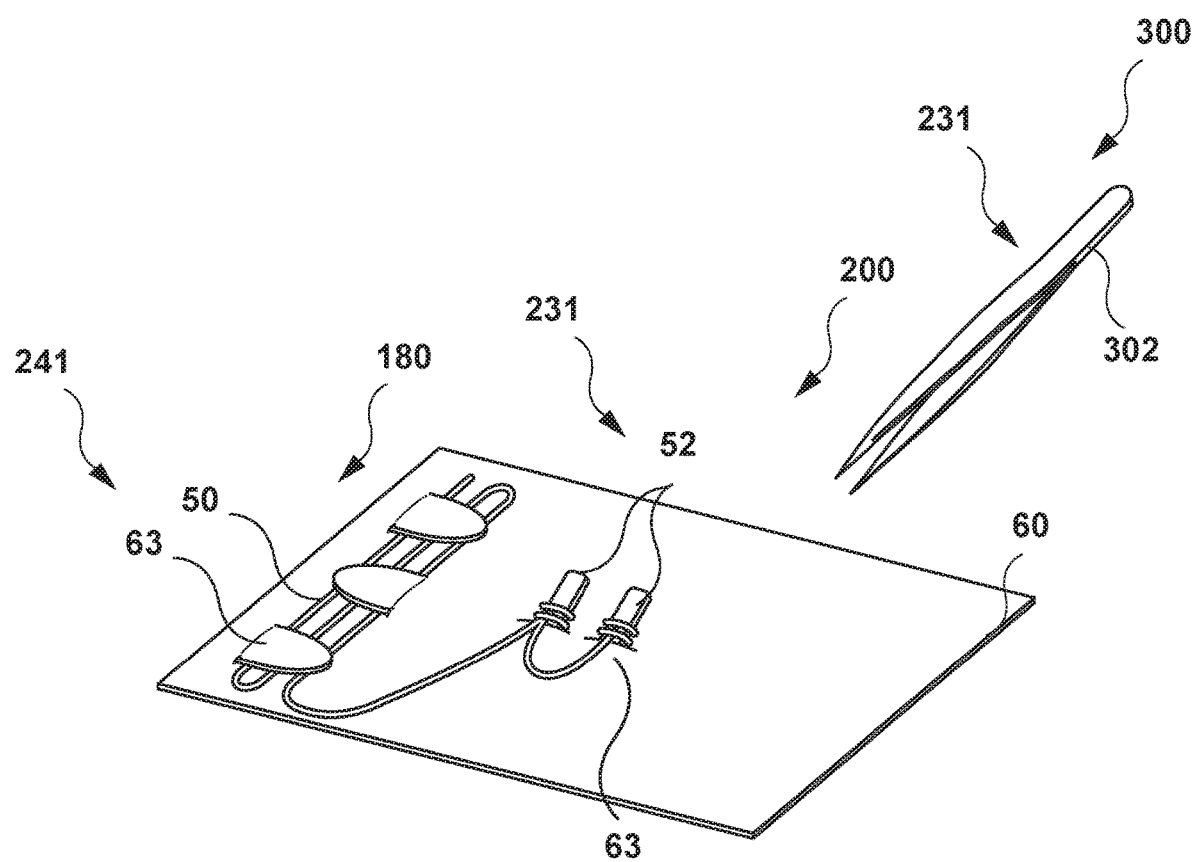

In some such examples, the closing device 180 may be loaded onto a delivery device with the use of one or more additional devices or instruments. These may assist in transfer of the closing device 180 from the cartridge 200 to the delivery device 100. The one or more devices may be used to remove one or more closing devices 180 from the cartridge 200 to place them onto the delivery device 100, or they may function to retain/hold the one or more closing devices 180 after they have been removed from the cartridge 200 to enable the one or more closing devices 180 to be loaded onto the delivery device 100 therefrom. As such, the tab loading/transferring feature 233 comprising an additional tool or device 302 for transferring the closing device 180 onto the delivery device or suture passer 102. In some such embodiments, as shown in FIG. 1F, where the loading device or cartridge 200 comprises a die card 60, the method may comprising using a tool or device 302 to grab suture tabs 52 and then insert them into the suture passer 102. In one such example, the tool or device 302 comprises tweezers and may be used to load tabs 52 (which in some examples may be suture tabs) into the suture passer 102. As illustrated in FIG. 1F, the implement or closing device 180 may be provided on a die card 60, where tabs 52 and the suture 50 may be secured to the die card 60 using a retaining means 63 such as flaps and/or cut-outs.

In some such embodiments, an indirect means may be provided to load the tabs 52 as shown in FIG. 1G. In some such examples, the tab loading/transferring feature 233 comprises an additional tool or device 302 for assisting in transferring the closing device 180 onto the delivery device or suture passer 102. In some such examples, the tab loading/transferring feature 233 comprises a means to temporarily hold the one or more tabs such as a tertiary device 310. In some such embodiments, a method of the present invention comprises a first step of placing the tabs 52 [such as a pair of tabs 53] from the loading device or cartridge 200 [such as from the die-card 60] onto a tertiary device 300. For example, the tabs 52 may be placed from the loading device or cartridge 200 onto holes within the tertiary device 310. In some such examples, the tertiary device 310 comprises a retractor 70 or a portal 80 that is used to access the tissue site, as shown in FIGS. 1G and 1H. This may help provide the delivery device 100 with ease of access to multiple closing devices 180 [such as multiple tabs]. For example, a method of the present invention provides a second step where the loading device such as a suture passer 102 grabs the tabs from the tertiary device 310. As such, placing the tabs 52 on the tertiary device 310 may enable the delivery device 100 [for example a suture passer 102 comprising a needle 110] to be loaded sequentially or concurrently with multiple closing devices 180. The loading device such as a cartridge 200 functions to hold the tabs in place for the suture passer 102 to go over them to load them therein. More specifically, this may allow for multiple closing devices 180 to be loaded onto the delivery device 100 to enable deployment of more than one closing device 180 to close a defect for example within an intervertebral disc, to perform herniated disc repair. In other words, this may provide the benefit for providing easy access for providing multiple stiches using the same delivery device using multiple closing devices 180. Still alternatively, in another example, the tertiary device 310 comprises a support device 90 comprising a finger ring clip that holds a number of tabs 52 that the surgeon may easily access. Still alternatively, the tertiary device may comprise any other stationary surgical tool that could hold the tabs 52.

Active Loading Devices [Using a Push Mechanism]

In some embodiments of the present invention, an active means is provided within the loading device or cartridge 200 to actively load the closing device 180 onto the delivery device 100.

Direct Mechanism

In some such examples a direct mechanism is provided for loading the closing device 180 onto the suture passer 102. In other words, the closing device 180 is loaded directly onto the suture passer 102 without requiring the use of an additional device.

In one such example, the tab loading/transferring feature 233 comprises a push mechanism. With reference to FIG. 2A, the cartridge 200B comprises a tab holding feature 231 comprising a seat 230 for holding the one or more tabs 52, such as a pair of tabs 53 therein. In the specific example shown, the seat 230 defines a tab holding passage 232 for holding the one or more tabs 52. In the example, the seat 230 defines a slider 238 that is moveable within a housing 201 of the cartridge 200. Specifically, the tab loading/transferring feature 233 comprises a push rod 234 comprising a spring-biased mechanism where the push rod 234 additionally comprises a spring 235.

The cartridge 200B comprises a delivery device engagement or alignment feature 220 that defines a delivery device receiving passage 222 in communication with the tab holding passage 232 for receiving a portion of the delivery device 100 therein. In one such example, as shown in FIG. 1E, the delivery device 100 comprises the suture passer 102, as described herein above. In one such example, the delivery device alignment feature 220 comprises a needle engagement or alignment feature for co-operatively engaging with the needle 110 of suture passer 102 to enable transfer of the one or more tabs into the needle 110. The delivery device engagement feature 220 such as a needle engagement feature comprises a delivery device receiving passage 222 such as needle receiving passage in communication with the tab holding passage 232 for receiving the needle 110 therein [as further illustrated in FIG. 2C]. More specifically, the slider 238 comprises a feature for mating with the delivery device 100. In the case where the delivery device 100 comprises a needle 110, wherein the needle 110 is configured to mate with the slider 238. The slider 238 comprises a face that is configured to mate with a face of the needle (or in other words needle face). The slider 238 is configured to slide within the housing 201 upon advancement of the needle 110 therein to interact with the spring biased mechanism of the push rod 234 that is configured to be pushed to depressed via the needle 110 to enable the one or more tabs 52 to be deployed by the push rod 234 onto the needle 110. In some such examples, as discussed previously, the spring 235 is depressed to facilitate loading of the tabs 52 onto the needle 110. The spring 235 may help ensure that sufficient force is applied to load the tabs 52.

As shown in FIG. 2B, the cartridge 200 additionally provides an opening 228 defined by the needle receiving passage. The opening 228 provides a clearance for the needle 110 as well as a device stop or protrusion 125 on the needle 110 that engages with the cartridge 200 to assist with positioning of the needle 110 within the cartridge 200. As such the push mechanism comprises a spring biased push rod 234 for engaging with the one or more tabs 52 for loading them onto the delivery device 100. As such, a direct push mechanism comprises a push mechanism comprising a spring biased push rod for engaging with the one or more tabs for loading them onto the delivery device.

Alternatively, in some examples, as shown in FIG. 2C, the cartridge may comprise a pull mechanism where the tabs are coupled to the tether 54 and suture 50 comprising the locker strand 58 and service loop 56. In some examples, the extra suture such as the service loop 56 and the locker strand 58 are managed external to the suture passer 102 using an affixing means 65 ones the tabs and suture 50 are loaded onto the suture passer 102. In one example, the locker strand 58 is provided with an affixing means such as a clip 64 within the cartridge 200. The locker strand 58 may be coupled to the suture passer 102 using the affixing means comprising a clip 64 that attached to a handle 130 of the suture passer 102. Similarly, the tether 54 may be provided with a clip 64 within the cartridge 200 to enable it to be coupled to the suture passer 102 after loading of the closing device 180 onto suture passer 102. In one such example, the pull mechanism comprises pulling the tether to load the tabs 52 into the suture passer 102.

In accordance with a method of the present invention, a method is provided for treating an intervertebral disc, where tabs 52 of the closing device 180 are loaded into a delivery device 100 at the point of use using the cartridge 200, and the method provides for using the delivery device 100 to close a defect of the intervertebral disc by means of the closing device 180. The method may additionally comprise loading the tether 54 and suture 50 such as the suture locker 58 onto the suture passer 102. The method of treating an intervertebral disc by loading tabs 52 and/or additionally tether 54 and suture 50 [such as suture locker 58] may be performed using, any of the loading devices for loading one or more components of the closing device 180 onto the delivery device 100 and/or the tissue or tissue site 10, and methods described herein in the present application. The components of the closing device 180 may comprise tabs 52, tether 54 and suture 50 [comprising service loop 56 and locker 58].

Indirect Mechanism

In accordance with some embodiments of the present invention, an indirect means is provided for loading the closing device 180 onto the suture passer 102. In other words, the closing device 180 is loaded indirectly onto the suture passer 102 using a push mechanism.

Figure 2D:
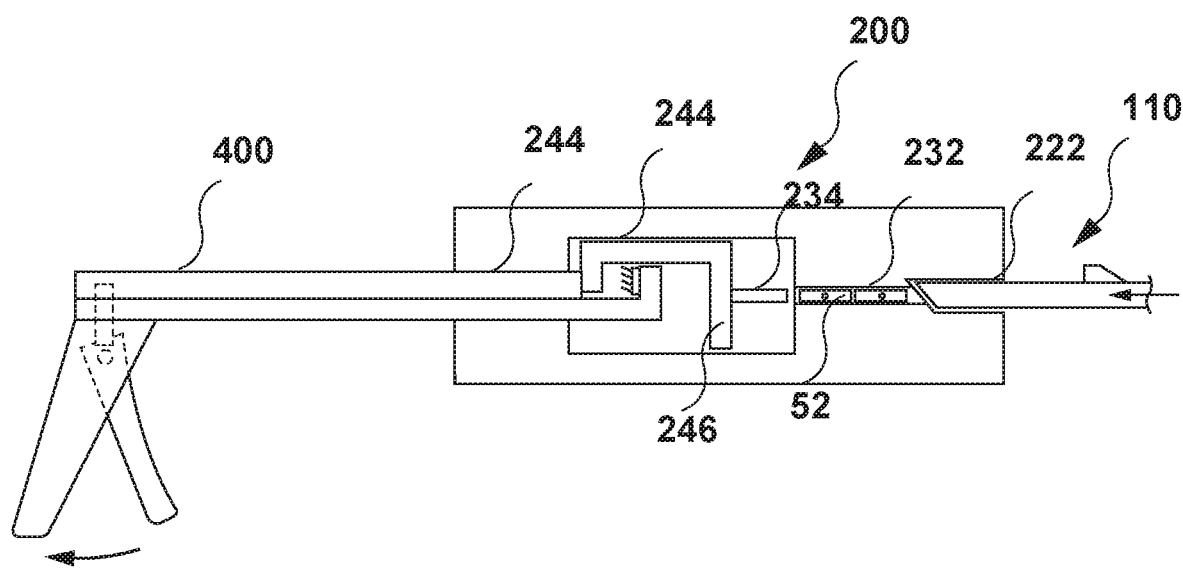
Figure 2E:
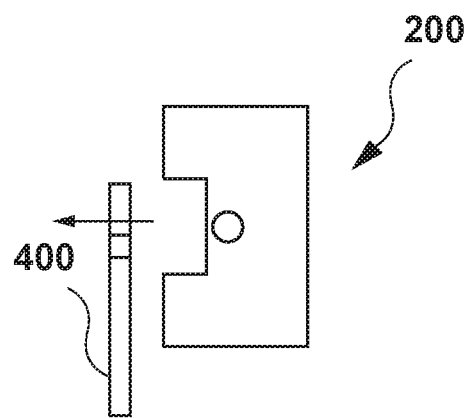

In one such example, an indirect push mechanism is provided, as shown in FIG. 2D. A cartridge 200 is provided that defines an instrument receiving passage 244 (which may alternatively be referred to as a passage/cavity herein) for receiving an instrument 400 therein for pushing the one or more tabs 52 for loading them onto the delivery device 100. The instrument receiving passage/cavity 244 is in communication with the tab holding passage 232 and the needle receiving passage, in some examples both also defined by the cartridge 200. In one example, the cartridge 200 comprises an arm 246 comprising a push rod 234, positioned within the instrument receiving passage/cavity 244 for co-operatively engaging with the instrument 400 and being moveable within the instrument receiving passage/cavity 244 for pushing the one more tabs 52 for loading them onto the delivery device 100. In one specific example, as shown in a top view in FIG. 2E, the cartridge is loaded from the side onto the instrument 400. In the specific example shown, the instrument or secondary instrument 400 comprises a Kerrison device. In one such example, instrument receiving passage/cavity 244 defines an entry/entry passage for the kerrison. Alternatively, the instrument receiving passage/cavity 244 defines an entry passage for receiving any other secondary instrument 400.

In accordance with a method of the present invention, the needle 110 of the suture passer 102 is advanced into the cartridge 200/kerrison 400 assembly. The cartridge 200 provides for movement of a component such as the arm 246 within the cartridge 200 to enable transfer of tabs 52. Once the needle 110 is received within the needle receiving passage, the kerrison is actuated to push the arm 246 and thus the push rod 234 to push tabs 52 into the needle 110. The needle 110 may then retracted one the tabs 52 have been loaded therein. In one such example, the loading/transferring feature comprises an instrument receiving passage or entry passage 244 for receiving an implement or tool such as an instrument 400 there-through for pushing the one or more tabs onto the delivery device, in combination with the moveable arm 246 comprising a push rod 234. In other words, a loading device is provided that comprises a cartridge 200/instrument 400, where the loading/transferring feature comprises one or more of an instrument 400, the entry passage 244 and the arm 246. In one such example, the cartridge 200 additionally defines an exit passage [which may be defined by the tab holding passage 232] to enable the one or more tabs 52 to be transferred onto the delivery device 100. In one such example, the tab loading/transferring feature may additionally comprise the entry passage 244 and exit passage.

Direct Mechanism

In still another example, a direct mechanism is provided for loading the closing device 180 onto the suture passer 102. In other words, the closing device 180 is loaded directly onto the suture passer 102 without requiring the use of an additional device.

In another embodiment of the present invention as shown in FIG. 2F, a direct push mechanism may be provided. The push mechanism comprises a pre-loaded spring that is releasable upon advancement of the delivery device for automatically pushing the one or more tabs for loading them onto the loading device.

In one such example, as shown as FIGS. 2F and 2G, a cartridge 200 is provided that defines a magazine 202 that defines a seat 230 defining a tab holding or retaining passage 232 comprises one or more tabs 52 therein. In one such example, the tab loading or transferring feature 233 comprises a push rod 234 comprising a spring-biased mechanism where the push rod 234 additionally comprises a spring 235. In one such example, the spring comprises a pre-loaded spring 235 that is provided initially in a pre-compressed or biased position 235A. The spring 235 is releasable upon advancement of the delivery device 100 such as the needle 110 of the suture passer, for automatically pushing each of the one or more tabs 52 for loading them onto the delivery device 100. In one such example, the needle 110 engages a lever to release the pre-loaded spring 235 to allow it to move into its expanded or unbiased position 235B, to enable the push rod 234 to advance within the tab holding/retaining passage 232 to push the tabs 52 into the needle 110, as shown in FIG. 2H.

In one such example of a method of the present invention, the cartridge 200 may be used to deposit/place the magazine 202 for ease of access for the user such as the physician in order to streamline the procedure. In some such examples, the physician may place the magazine 202 beside a tissue site for example at a tissue site 10 such as at the site of defect to be treated using the closing device or at a surface accessible to the user such as a surgical surface 12 such as a table.

In another example, a cartridge 200 is provided, as shown in FIG. 2I, the cartridge may comprises multiple holes or openings [each associated with a magazine 202]. The cartridge 200 carries multiple sets of one or more tabs 52 [each in a magazine 202] wherein the cartridge 200 comprises multiple pre-loaded springs 235 [each associated with a magazine 202]. Each of the springs 235 being releasable upon advancement of the delivery device for automatically pushing each of the one or more tabs for loading them onto the delivery device 100. As such, a cartridge 200 is provided with multiple holes for multiple loadings on the table. As such, the user may not need to retract device to reload.

Active Loading Devices [Using a Pull Mechanism]

Figure 3A:
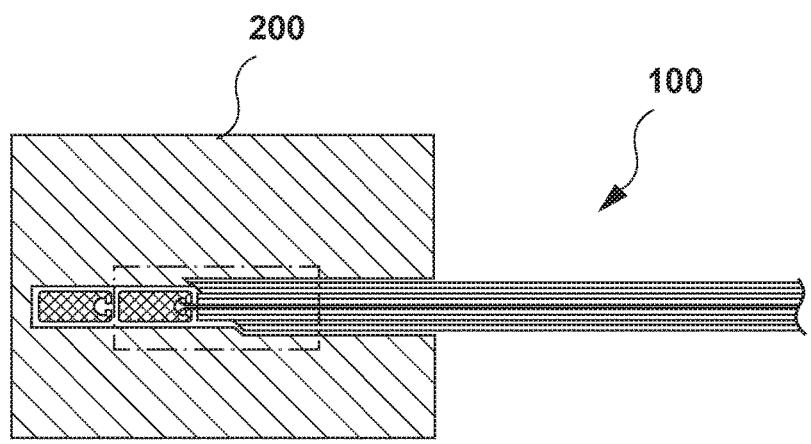
Figure 3B:
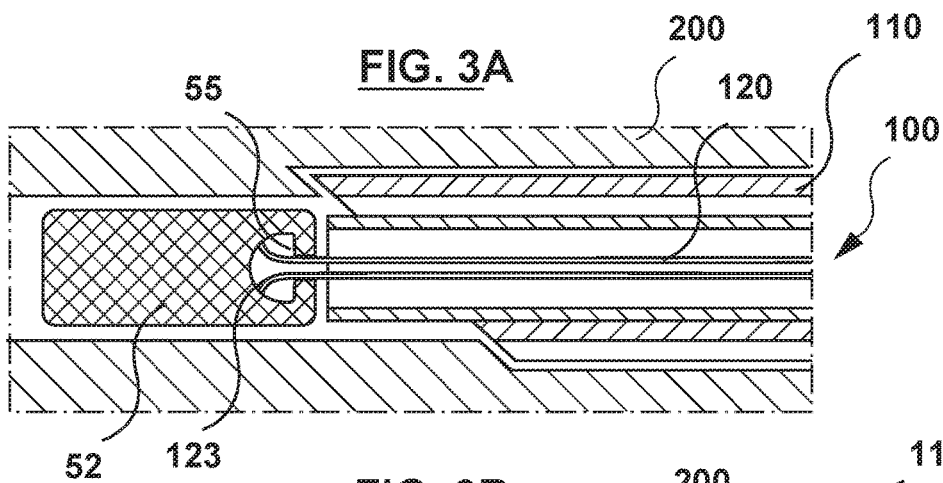
Figure 3C:
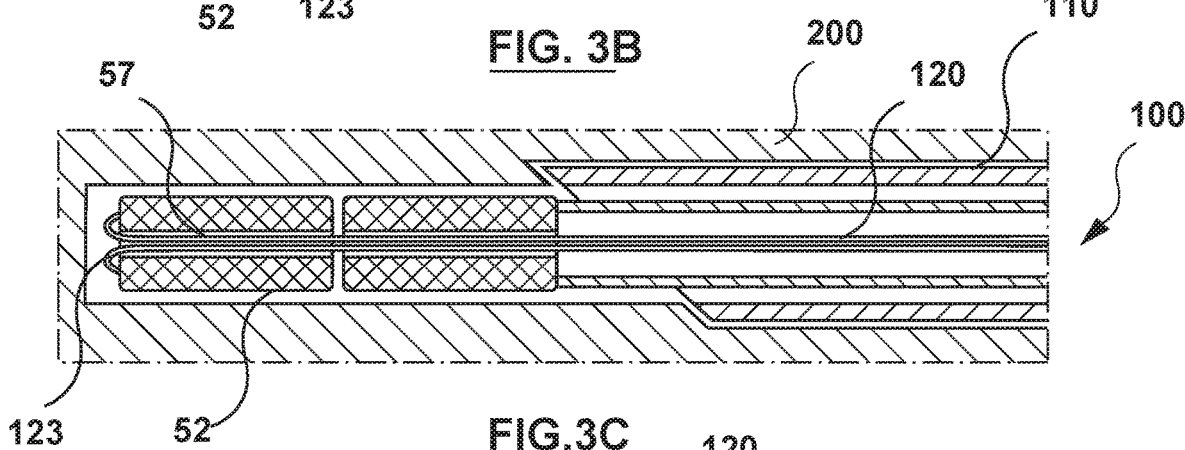
Figure 3D:
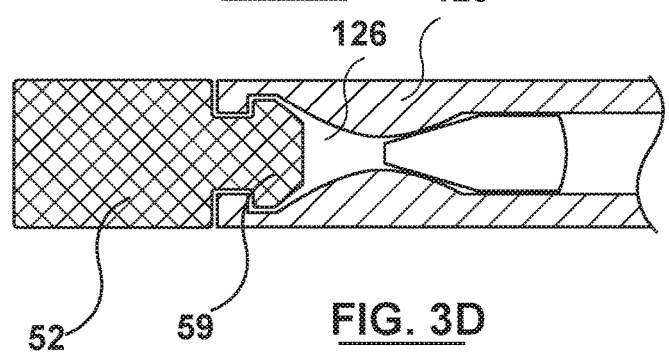

In another embodiment of the present invention, as shown in FIGS. 3A-3D, a direct pull mechanism is provided where the tabs 52 are loaded from the cartridge 200 directly onto the delivery device 100 comprising the suture passer. In one such example, the cartridge 200 defines a seat 230 that defines a projection 236 for holding the one or more tabs 52 thereon. In some such embodiments, the pull mechanism comprises a stylet 120 housed within the delivery device 100 that is configured to engage the one or more tabs 52 for loading them onto the delivery device 100. As shown in FIGS. 3B to 3D, the stylet comprises features for grabbing the tabs 52. In some examples, the stylet 120 comprises projections for engaging with the tabs 52.

In some examples, as shown in FIG. 3B, the tab 52 defines a cavity 55 for receiving a portion of the stylet 120 therein for engaging therewith. In one such example, the stylet 120 comprises one or more projections or retention features 123, such as one or more grippers that flare out to engage with and grab the one or more tabs 52. In a specific example, the stylet 120 flares out and grabs a first tab. As the stylet 120 pulls the first tab, the first tab pulls in the second tab that is coupled thereto.

In some examples, as shown in FIG. 3C, the one or more tabs 52 each define a passage 57 there-through for receiving the stylet 120 therein. Similarly, the stylet 120 comprises one or more projections defining a retention feature 123, such as one or more grippers or flares that flare out to engage with and grab the one or more tabs 52. In one such example, the stylet 120 (such as an inner stylet) goes through both tabs 52 and grabs both.

Alternatively, as shown in FIG. 3D, the one or more tabs 52 comprise one or more projections 59 that engages with a cavity 126 within the stylet 120 to engage with and grab the one or more tabs 52. In one such example, the stylet 120 snaps onto the first one of the tabs 52 allowing the stylet 120 to pull in both tabs 52. The inner stylet 120 then releases the stylet grip.

Indirect Mechanism

In accordance with some embodiments of the present invention, an indirect means is provided for loading the closing device 180 onto the suture passer 102 using a pull mechanism. In other words, the closing device 180 is loaded indirectly onto the suture passer 102 using a pull mechanism.

In one such example, as shown in FIG. 3E, the cartridge 200 defines a magazine block 202. The cartridge 200 deposits the magazine block adjacent the defect or to the edge of a surgical instrument such as a retractor. As such, in one example, the cartridge 200 comprises a coupling means for coupling to a surgical tool. More specifically, the cartridge 200 comprises a coupling means for coupling to a surgical tool taken from a portal and a retractor. As shown in FIG. 3F, the magazine or magazine block 202 defines a base or base portion 204 and a pull tab or knot slider 206. In one such example, the tab loading/transfer feature 233 comprises a pull mechanism. In one such example, a pull tab such as a knot slider 206 that is coupled to the one or more tabs 52, the pull tab 206 being detachably coupled to a base portion 204 of the cartridge 200, wherein the pull tab 206 and the base portion 204 of the cartridge 200 define the delivery device receiving passage 222 for receiving the delivery device 100 therein and wherein the pull tab 206 is releasable or detachable from base portion 204 to pull the one or more tabs 52 to load the one or more tabs 52 into the delivery device 100, as shown in FIG. 3G. The method involves using cartridge 200 to deposit magazine 202 to defect site or to the edge of a surgical instrument, inserting needle 110 into the delivery device receiving passage 222, and pulling the knot slider 206 to pull in tabs 52 into the needle 110.

Active Mechanism—Eat

Direct Mechanism

In some such examples a direct mechanism is provided for loading the closing device 180 onto the delivery device 100 such as the suture passer 102. In other words, the closing device 180 is loaded directly onto the suture passer 102 without requiring the use of an additional device. In one such example, as shown in FIG. 4A, the cartridge 200 provides the tabs 52 such that an eat mechanism is employed to load the tabs 52 onto the cartridge 200, where the delivery device 100 is configured to be advanced over the tabs 52 to capture or retain them therein. In one such example, the cartridge 200 comprises a seat 230 defining a projection 229 for holding the one or more tabs 52 thereon, as additionally shown in FIG. 4B. In one such example, a direct transfer mechanism is provided [for the tab loading/transferring feature 233] where the delivery device 100 is directly loaded using the cartridge 200. In one such example, the tab loading/transferring feature 233 comprises a push mechanism. In one specific example, the push mechanism comprises an eat-push mechanism. In other examples, an indirect transfer mechanism is provided [for the tab loading and transferring feature 233] where the delivery device 100, such as suture passer 102, is indirectly loaded (or loaded indirectly) using the cartridge 200. For example, the closing device 180 is loaded indirectly onto the delivery device 100, such as the suture passer 102, from the cartridge 200 by the use of one or more additional or intermediate devices.

As specifically shown in FIG. 4A, the cartridge 200 comprises a tab retention slider 239 where the tab retention slider 239 defines the seat 230 comprising a projection 229 for holding the tabs 52 thereon, wherein the projection 229 comprises a tab retention means such as a tab retention stylet 226 that extends into the delivery device receiving passage 222 for enabling the delivery device 100 to capture the one or more tabs 52 therein. In a specific example, the tab retention slider 239 comprises a feature for mating with the delivery device 100. In one such example, the delivery device 100 comprises a needle 110, wherein the needle 110 is configured to mate with the tab retention slider 239 that comprises a spring biased mechanism comprising a spring 235. The cartridge of the present invention additionally comprises a push rod 234, where the tab retention slider 239 is slidable there-along. The tabs 52 are positioned against the push rod 234. In a specific example, as shown in FIG. 4A, the tab retention slider comprises a face 237 that is configured to mate with a distal face 117 of the needle 110. In one such example, the tab retention slider 239 comprises a spring biased mechanism that is configured to be depressed via the needle 110 to enable the one or more tabs 52 to be deployed from the stylet 226 onto the needle 110. In the specific example shown, the push rod 234 additionally comprises a retention feature 236' at its distal to retain one or more tabs 52 thereon. In one such example, the push rod 234 is flared at its distal end. In one such example, stylet 226 comprises one or more retention wires 227, as shown in FIGS. 4D and 4E, for holding the tabs 52. In one such example, the tab retention slider 239 comprises one or more holes 225 for receiving the one or more retention wires 227 therein, as shown in FIG. 4C. In one such example, as the needle 110 is inserted into the delivery device receiving passage 222 it is advanced till the distal face 117 of the needle 110 engages with the face 237. This enables the needle 110 to push the tab retention slider 239 along the push rod 234 allowing the spring 235 to be depressed and the tab retention slider 239 to retract. This enabling the tabs to be freed from the tab retention stylet 226 to be deployed therefrom to allow the needle 110 to capture them therein. The push rod 234 assists in deployment of the tabs 52 as the tabs 52 are positioned in abutting contact with the push rod 234. As such, the push rod may prevent the tabs 52 from being retracted with the stylet 236 as it retracts within the cartridge 200.

Figure 4I:
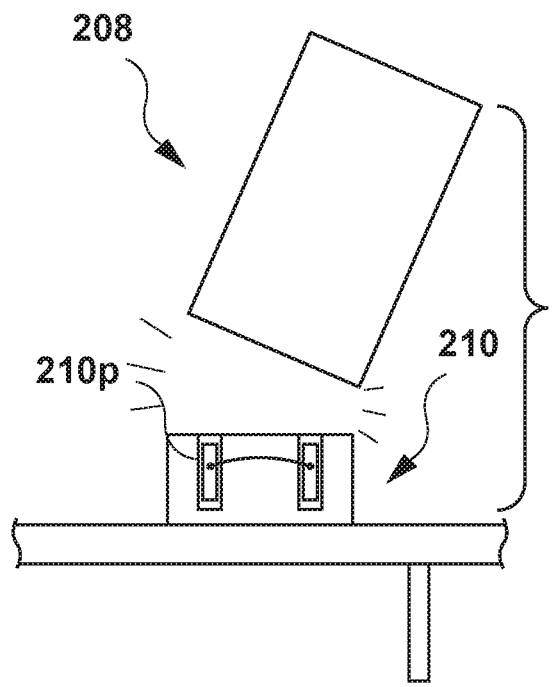
Figure 4J:
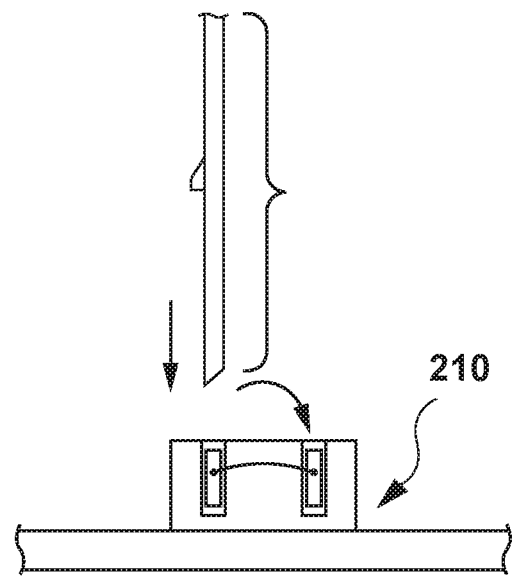

In another embodiment of the present invention, as shown in FIGS. 4F and 4G, an indirect means is provided to load tab 52 onto a delivery device 100. In one such embodiment a cartridge 200 is provided comprising a suture plug. In one example a cartridge 200 is provided comprising a cartridge body 208 and a suture plug 210 that is detachable from the cartridge body 208 to be deposited adjacent a surgical site for ease of access. In some such embodiments, the suture plug 210 may be understood to be an attachment to the cartridge, or a "cartridge attachment". As additionally shown in FIG. 4H, the cartridge attachment 210 comprises the seat 230 defining one or more tab holding passages 232 for holding the one or more tabs 52 therein, and a delivery device receiving passage 222 for that receiving the delivery device 100 therein in communication with the seat 230 for enabling the tabs to be received therein. As shown in FIGS. 4H, 4I and 4J, in some such examples, the one or more tab holding passages 232, comprise a pair of tab holding passages 232*p* [Specifically, 232A, 232B] for holding a pair of tabs 53. In one such example, a method of the present invention may comprise depositing the detachable cartridge attachment/suture plug 210 to a surgical site such as a tissue site 10, and advancing the needle 110 into the cartridge to allow the needle 110 to collect the tabs 52 from the cartridge attachment/suture plug 210 and passing the tabs into the tissue site 10 to pass a suture there-through for example for carrying out a stitch.

Figure 4L:
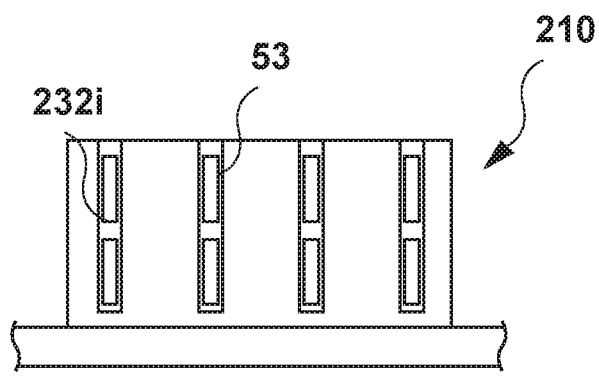
Figure 4L:
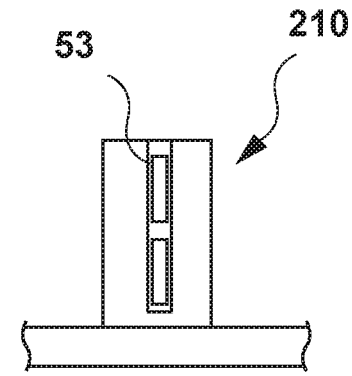

Alternatively, in accordance with another embodiment of the present invention, a method is provided as shown in FIG. 4I, where the cartridge 200 is used to deposit the cartridge attachment/suture plug 210 at a surgical surface 12. The suture passer 102 is then advanced into the cartridge 200 to load the tabs 52 therein, and then the suture passer 102 is taken to the surgical tissue site or tissue site 10. In some such examples, as shown in FIG. 4*k*, the cartridge attachment 210 comprises a multi-stich version with multiple passages 232*i* for holding multiple pairs 53 of tabs 52 therein. Alternatively, a single plug version may be provided where passage 232*i* may be provided for holding a pair of tabs 53 therein as shown in FIG. 4L.

Figures 4M, 4N:
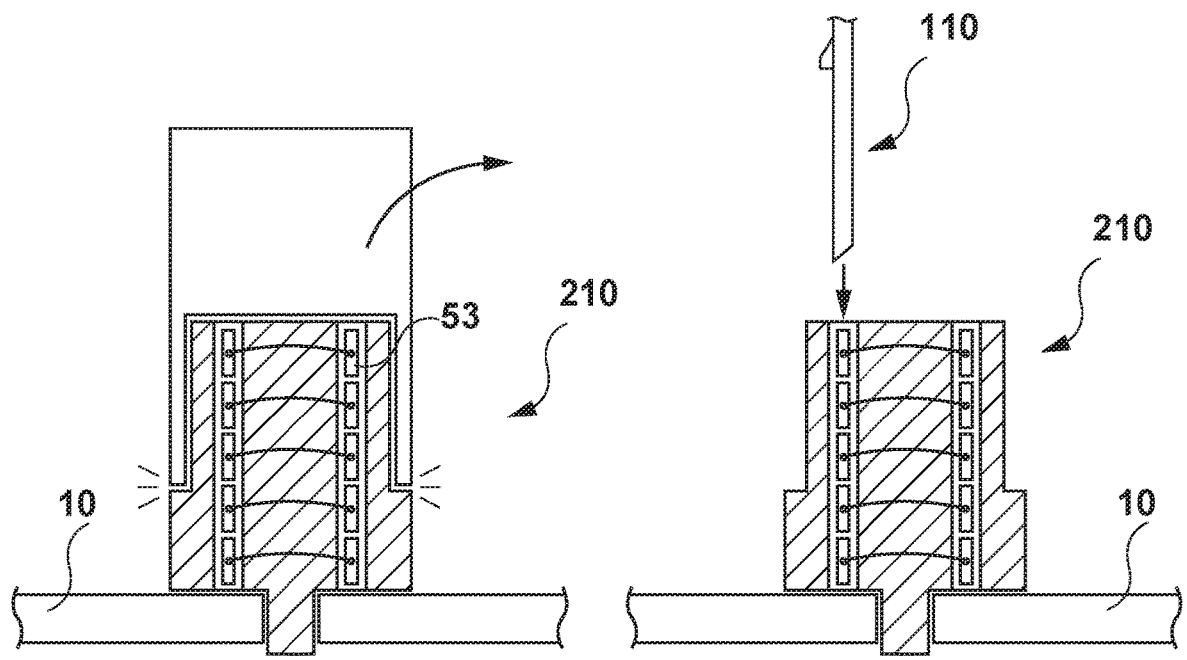
FIGS. 4M-4P are illustrations of alternate loading devices in accordance with various embodiment of the present invention to enable loading of multiple closing devices into the delivery devices and deployment thereof thereafter for depositing multiple closing devices into tissue.
Figures 4O, 4P:
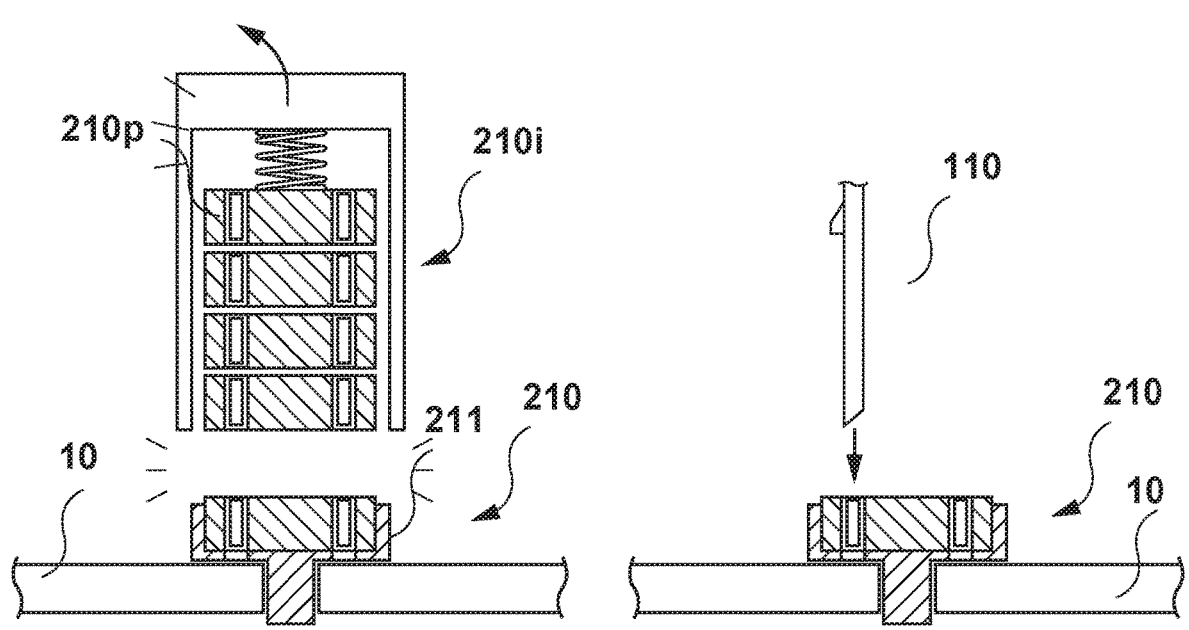

In one such example, the cartridge attachment/suture plug 210 may comprise tab holding passages [232A, 232B] for holding multiple pairs 53 of tabs 52, as shown in FIG. 4M. The cartridge 200 may deposit the multi-suture cartridge attachment or suture plug 210 [or in other words a magazine-plug] to the surgical site. In one such example, the suture plug 2110 may be deposited at a surface for ease of access for the user, for example at a tissue site 10 at a defect, as shown in FIG. 4N. The needle 110 may be advanced to grab each of the pairs of tabs 53. As such, the suture passer 102 loads tabs 52 and may perform multiple stiches from one plug 210. Still alternatively, the cartridge attachment or suture plug may comprises multiple plugs 210*i*, where each cartridge attachment or suture plug 210 defines a pair of tab holding passages 232*i* [232A, 232B], and is configured to be released independently, for example, adjacent a tissue site 10 to enable loading of the delivery device 100. In some such examples, the cartridge 200 comprises base plug or plug holder 211 that is deployable to support the cartridge attachment member or suture plug 210 thereon upon depositing of the cartridge attachment member or suture plug 210.

As such, in accordance with an embodiment of the present invention, a cartridge body or magazine 208 of the cartridge 200 deposits one cartridge attachment or suture plug 210 to the surgical site, the suture passer 102 then loads the tabs 52 therein and performs one stitch. The spent suture plug 210 may be removed. The cartridge body or magazine 208 then deposits another suture plug 210 into the plug holder 211 for another stitch.

Figure 5D:
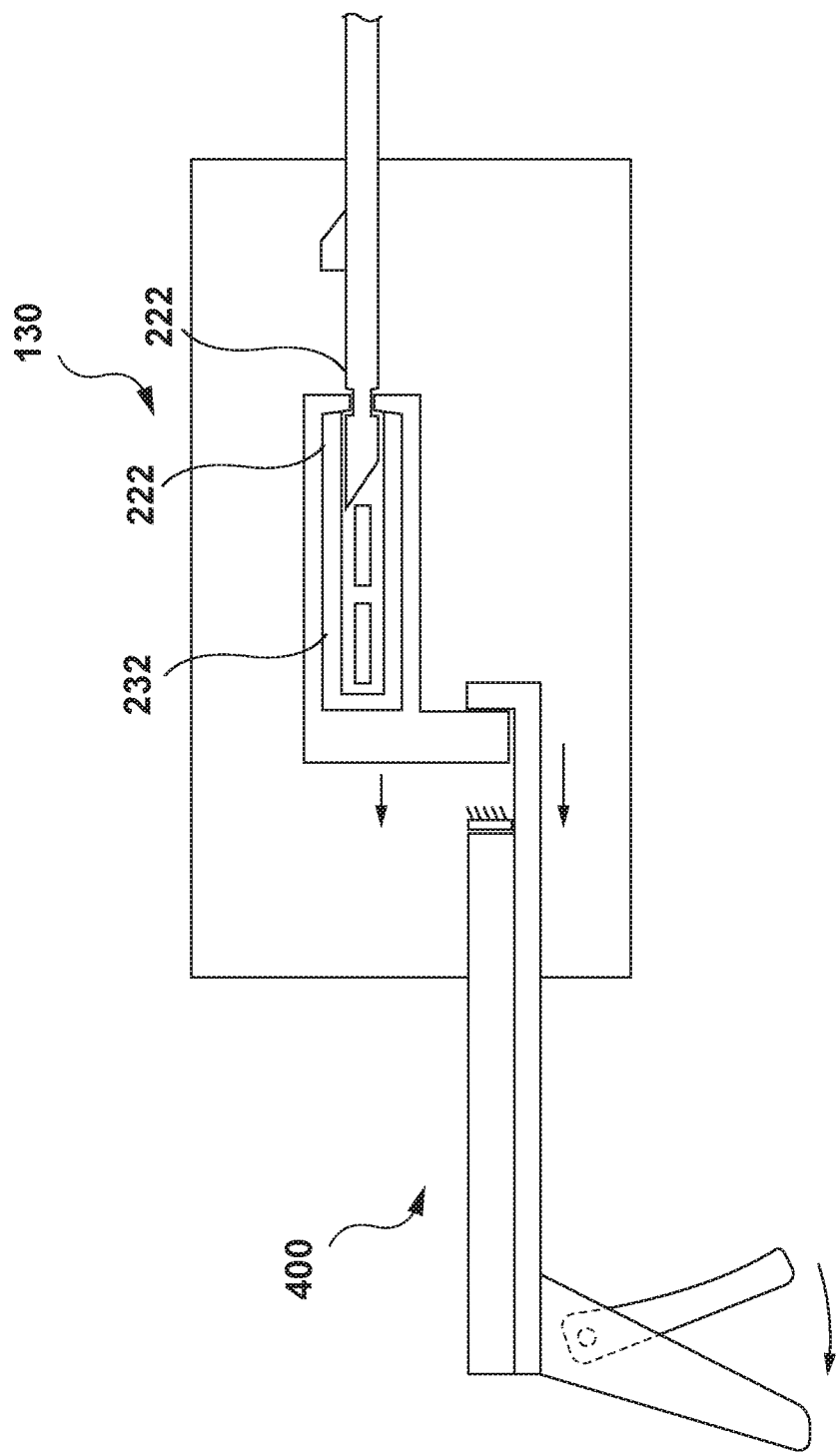
FIG. 5D is an illustration of a loading device employing an eat-pull mechanism in accordance with an alternate embodiment of the present invention.

In accordance with an embodiment of the present invention, a cartridge 200 is provided comprises a seat 230 defines a tab holding passage 232 for holding the one or more tabs 52. In one such example, the tab loading/transferring feature 233 comprises a pull mechanism. In one specific example, the pull mechanism comprises a pull-eat mechanism. In one such example, a direct mechanism is provided where the tabs 52 are loaded onto the delivery device 100 without the use of an additional device. The cartridge provides a pull-eat mechanism that comprises an actuator 249 that is configured to engage with a portion of the delivery device upon advancement of the delivery device into the delivery device receiving passage to advance the portion of the delivery device into the seat over the one or more tabs to capture the one or more tabs therein. In one such example, the needle comprises notches or holes 114, where the cartridge 200 comprises one or more linking arms, 262, where one of the arms 263 is configured to engage with the notches or holes 114 within the needle 110, as shown in FIG. 5C.

In one such example, the delivery device 100 comprises a needle 110 wherein the actuator of the pull mechanism comprises a lever mechanism 247 for converting a proximal actuation [F] of the actuator [for example by pulling it] into a distal movement of the needle 110 after reception of the needle 110 into the delivery device receiving passage 222 comprising a needle receiving passage, for advancing the needle 110 into the seat 230 to capture the one or more tabs 52 therein. As such, the needle 110 is configured to be pulled forward relative to the handle of the suture passer 102 to load the tabs 52 therein. In one such example, as shown in FIGS. 5A and 5B, the delivery device 100 is configured to be assembled in two parts. In one such example, the needle 110 is separable from a handle 130 of the suture passer 102 and is configured to be assembled at the point of use.

In another embodiment of the present invention, the cartridge defines a body or primary housing 201. The cartridge 200 additionally comprises a secondary housing 212 surrounding/defining the seat 230, the secondary housing 212 being positioned within the primary housing/body 201 in sliding engagement therein. The seat 230 defines a tab holding passage 232 for receiving and retaining one or more tabs 52 therein. The cartridge additionally defines a delivery device receiving passage 222 for receiving a delivery device therein wherein the delivery device receiving passage is in communication with the tab receiving passage. In the example shown, the primary housing 201 and the secondary housing 212 both define the delivery device receiving passage 222. The secondary housing 212 additionally comprises a delivery device engaging feature for engaging with the delivery device 100. In one such example, the needle 110 comprises a notch or holes 114, where the cartridge 200 comprises arms 263, for example with tabs 263' to engage with the notches or holes 114 within the needle 110. As such, in some embodiments of the present invention, the delivery device engaging feature comprises arms 263 extending from the housing for engaging with the delivery device 100, wherein the delivery device comprises a needle 110, and the needle 110 defines grooves or notches or holes 114 for engaging with the arms 263. In some examples, the delivery device receiving passage 222 defines a needle receiving passage terminating at a needle engaging feature that co-operatively engages with a needle face.

The cartridge 200 additionally comprises a secondary instrument receiving passage 222' for receiving a secondary instrument 400 there-through for interacting with the secondary housing 212 for pulling the secondary housing 212 proximally, for moving the delivery device 100 proximally over the one or more tabs 52 for receiving them therein. In one such example, the instrument 400 comprises a kerrison, and the method involves loading the cartridge 200 onto the kerrison, inserting the needle 110 into the cartridge 200, actuating the kerrison to grip the secondary housing 212, where the kerrison pull the needle 110 in and over the tabs 52.

Union Style Loading Devices

Figure 6A:
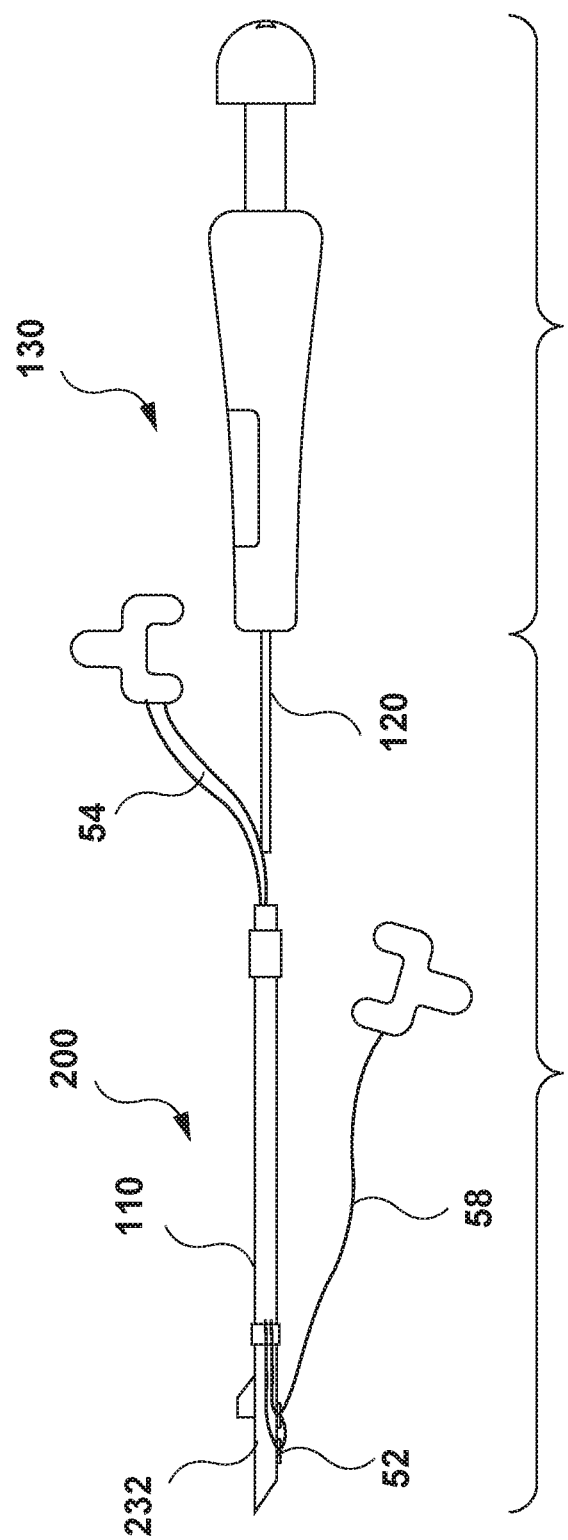

In some embodiments of the present invention, as shown in FIG. 6A, a cartridge 200 is provided that is configured to co-operatively engage with the delivery device 100 to form a part of the delivery device. In one such example, the cartridge 200 may be referred to as a union style loading device. In one such example as shown in FIG. 6B, a cartridge 200 is provided that comprises a needle 110 that defines the tab holding feature comprising a tab holding passage or recess 232, and the one or more tabs 52 are held within the tab holding recess 232. Additionally, the one or more tabs 52 have a tether 54 coupled thereto and suture 50 extends from the one or more tabs 52. More specifically, the suture 50 comprises a service loop 56 and a locker 58. The needle 110 additionally defines a proximal opening for allowing the tether 54 to exit there-through. The cartridge 200 additionally comprises a needle coupling feature such as a coupling means 132 for coupling the needle 110 to a handle 130 of the delivery device 100 to form the delivery device 100. The cartridge additionally comprises a tether coupling feature, such as an affixing means 65. In one example, the affixing means 65 comprises a clip 64. The tether coupling feature extends from the tether 54 for coupling to the handle 130. The cartridge 200 additionally comprises a suture coupling feature extending from one or both of the locker and the service loop for coupling to the handle 130. The suture coupling feature may also comprise an affixing means 65 comprising a clip 64. In one such example, upon assembly the stylet 120 coupled to the handle 130 is received within the needle 110. As such, in one example, the handle 130 comprises a stylet coupled thereto and the needle 110 defines a passage for receiving the stylet 120 there-through. As such, in some embodiments of the present invention, the cartridge 200 may comprise an entire shaft or needle 110 that is pre-loaded. Once the cartridge 200 is loaded onto the handle 130 and the stylet 120, it forms the delivery device 100. In some such embodiments, the delivery device 100 is actuable upon assembly to advance the stylet 120 to deploy the one or more tabs 52 from the needle 110 for treating tissue such as a defect.

Alternatively, as shown in FIG. 6B, the cartridge 200 additionally comprises the stylet 120. The stylet is coupled to and received within the needle 110 to form a needle/stylet assembly. In one such example, the cartridge defines the entire shaft [including the needle 110 and stylet 120] as well as a part of the handle/internal mechanism, where the handle 130 snaps onto the cartridge 200 to form the delivery device 100 and to facilitate usability of the cartridge 200 to use the tabs 52 to treat tissue for example at a defect. In one such example, the coupling means 132 comprises a distal handle that is provided on the cartridge to engage with and snap onto the handle 130. In one such example, the tether 54 and a tether cutter 67 are integrated into the cartridge 200. In one such example, post assembly, once the needle and the stylet have been coupled to the handle, the actuator 66 is actuable to deploy the one or more tabs 52 from the needle 110, where the tether cutter 67 cuts the tether 54 upon actuation to enable release of the tabs 52.

In an additional embodiment of the present invention, as shown in FIG. 6C, the cartridge additionally comprises the actuator 66. A handle 130 is provided with a hinge 133. The handle 130 in its open configuration is shown in FIG. 6D. The handle 130 folds onto the cartridge 200 to facilitate usability. As shown in FIG. 6E, the handle 130 hinges down over the cartridge 200. As such, in some embodiments, the cartridge 200 defines the entire shaft and the internal mechanism of the delivery device 100.

Figure 6F:
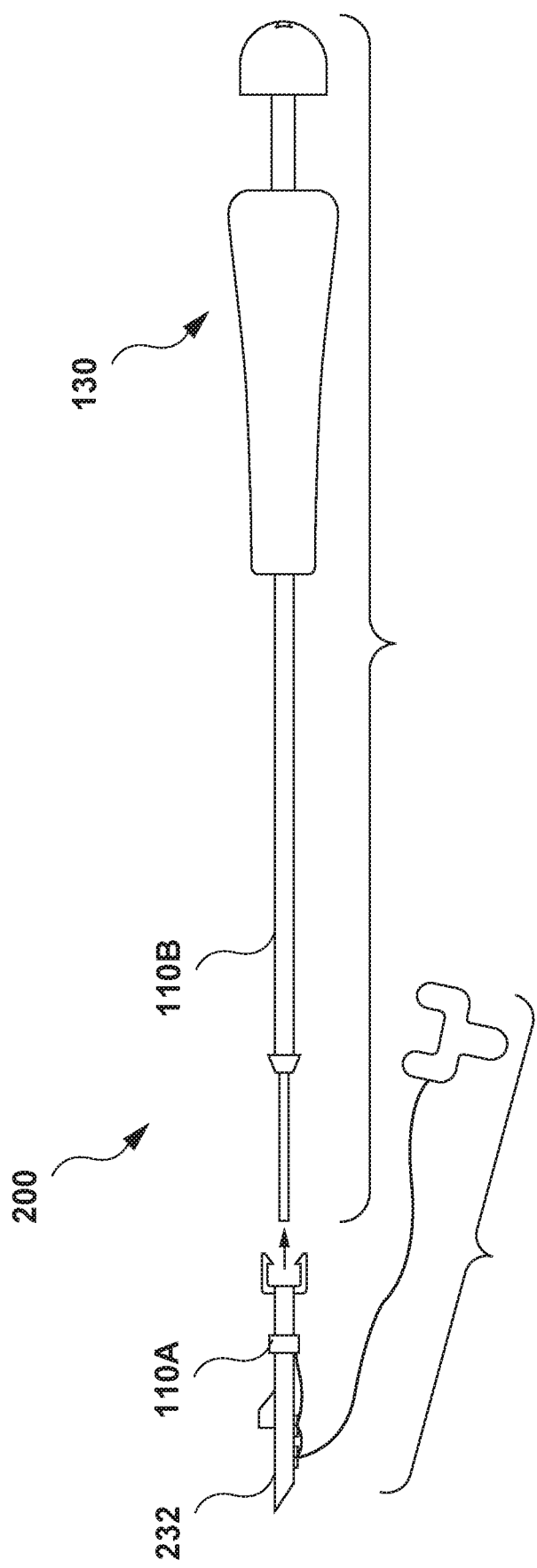

In an additional embodiment of the present invention, as shown in FIG. 6F, the delivery device 100 comprises the handle 130, and a stylet 120 coupled to the handle 130 and a proximal shaft 110B defining a proximal portion of the needle 110. A cartridge 200 is provided, where the cartridge 200 comprises a distal shaft 110A, and is configured to couple to the proximal shaft 110B upon assembly to form a needle shaft 110. In one such example, as shown, the distal shaft 110A defines a passage for receiving the stylet there-through. Similar to embodiments described herein above, the delivery device 100 is actuable upon assembly to advance the stylet 120 to deploy the one or more tabs 52 from the needle 110.

Figure 6G:
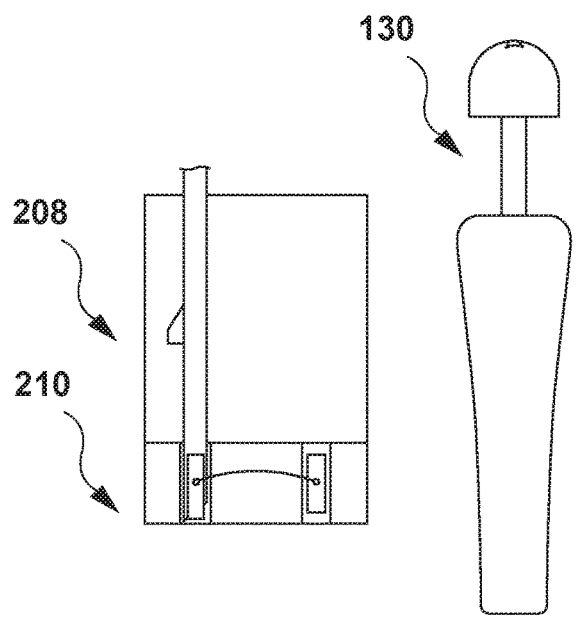
Figure 6H:
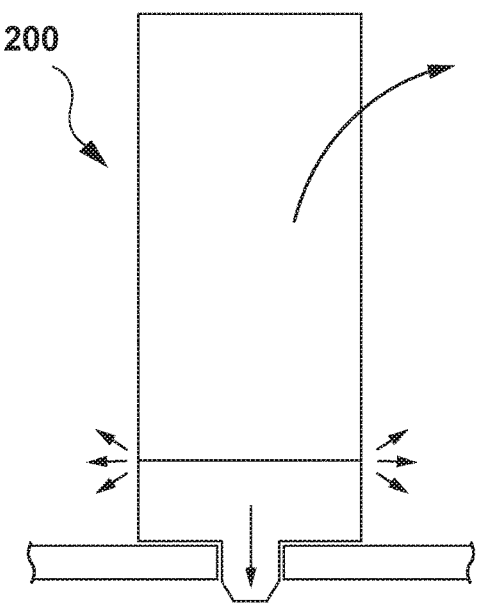
Figure 6I:
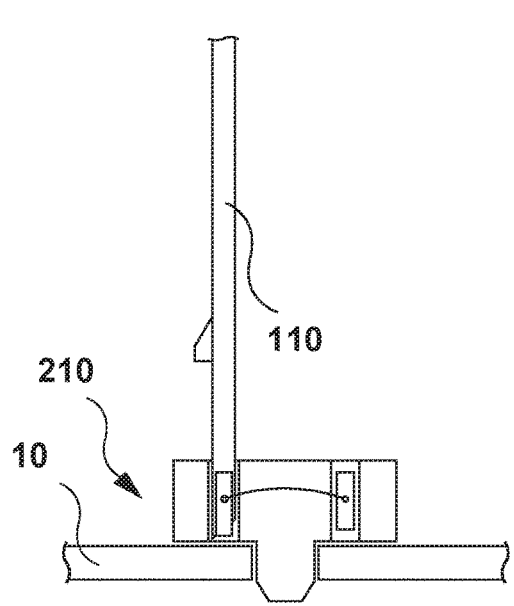
Figure 6J:
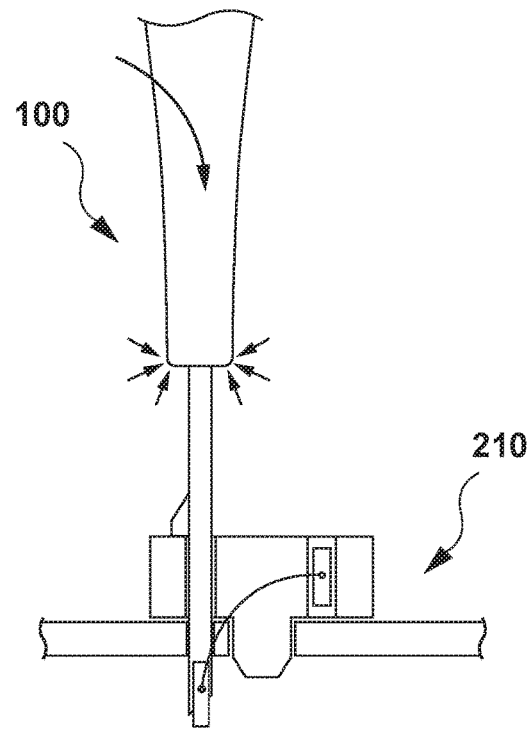

In one such example, as shown in FIG. 6G, where the cartridge 200 comprises the shaft such as the needle shaft of the needle 110, the cartridge may be similar to embodiments described herein above with respect to FIGS. 4F to 4P. In other words, the cartridge of example 67, wherein the needle is held within a housing of the cartridge. The cartridge comprises a cartridge body 208 and a cartridge attachment/suture plug 210 that is deployable for ease of access that contains the tabs 52 (that comprise suture tabs). As shown in FIGS. 6H and 6I, the cartridge body 208 is configured to deposit the suture plug/needle shaft of the needle 110 at the surgical site, such as at a tissue site 10 comprising a defect. The handle 130 can then be attached to the needle shaft of the needle 110 at the point of use to form the delivery device 100 and to facilitate use.

In some embodiments, as described herein below, one or more loading devices may be used to load the delivery device 100. In some such embodiments, two or more loading devices may be used in series or parallel to load the delivery device. In some such embodiments, where the cartridge comprises one or more loading devices for loading the closing device 180 onto the delivery device, the one or more loading devices comprise the tab holding feature and the tab loading/transferring feature for loading tabs onto the delivery device.

Figure 7C:
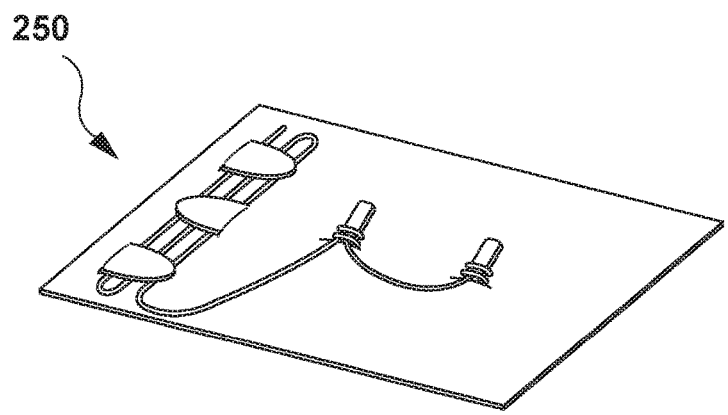
Figure 7D:
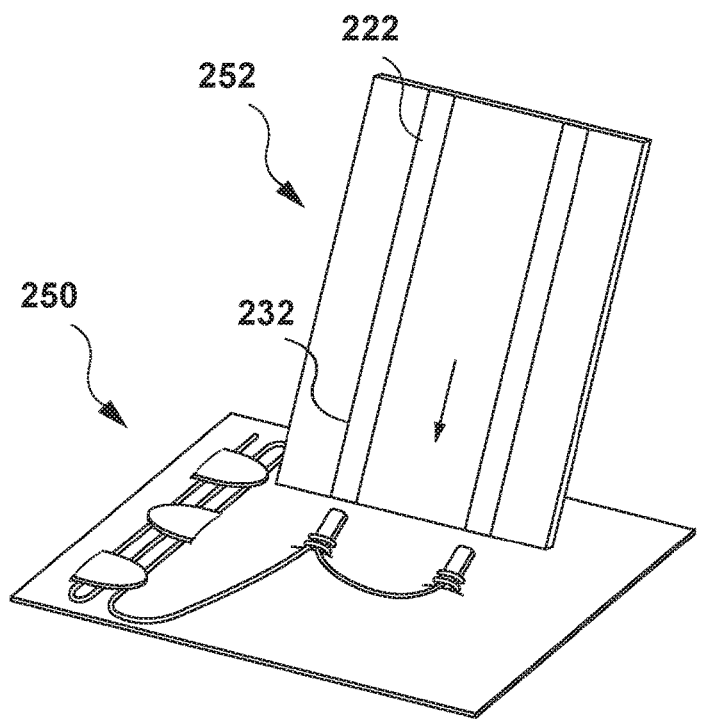
Figure 7E:
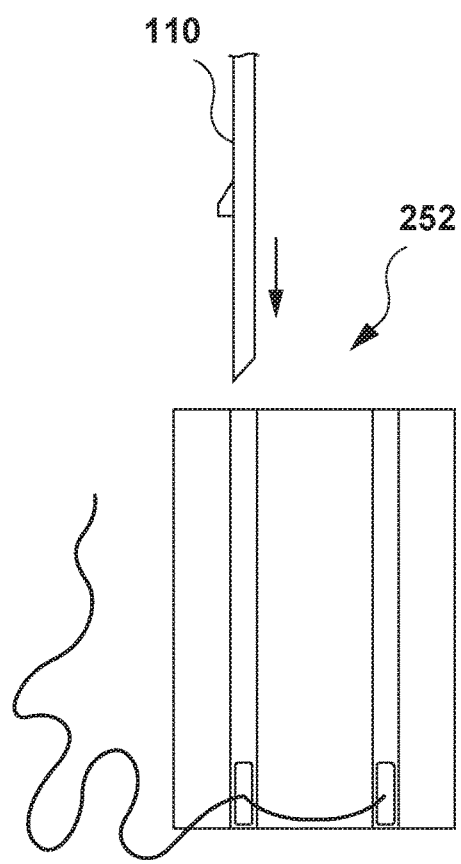

In one embodiment of the present invention, a first loading device 250 is provided, where the tabs 52 (comprising suture tabs) are provided on a die-card 60 or suture spool 62 [As shown in FIGS. 1B and 1C]. The method comprises providing a second loading device 252, as shown in FIGS. 7A and 7B, where a transfer plunger 256 of the second loading device 252 is used to grab tabs 52 from the first loading device 250 [die-card 60 or suture spool 62] to be retained therein. In one such example, the plunger 256 may hold tabs 52 via friction fit or a gripping material to hold tabs 52. The second loading device 252 defines a housing 201. The tabs 52 are retained within a tab holding passage 232 defined by the housing. The tabs 52 are then transferred from the second loading device 252 onto the suture passer 102. In one such example, the housing defines a mating feature for mating with the needle 110. In one such example, the needle 110 defines a bevel face or a distal face 117 and the housing defines a bevel face 217 for mating with the needle 110. Once the needle 110 is positioned against the housing 201, the plunger 252 is advanced to load the tabs 52 onto the suture passer 102. In one such example, a first loading device 250 may comprise a die card 60, where the die card 60 contains the tabs 52 (which in some examples are suture tabs) [FIG. 7C]. A second loading device 252 is provided that is configured to grab tabs/suture from the first loading device 250 [FIG. 7D]. The second loading device 252 defines delivery device receiving passages 222 that are in communication with the tab holding passages 232, which enables the needle 110 of the delivery device 100 to be advanced therein to allow the tabs 52 to be loaded into the needle 110 [FIG. 7E].

Figure 7F:
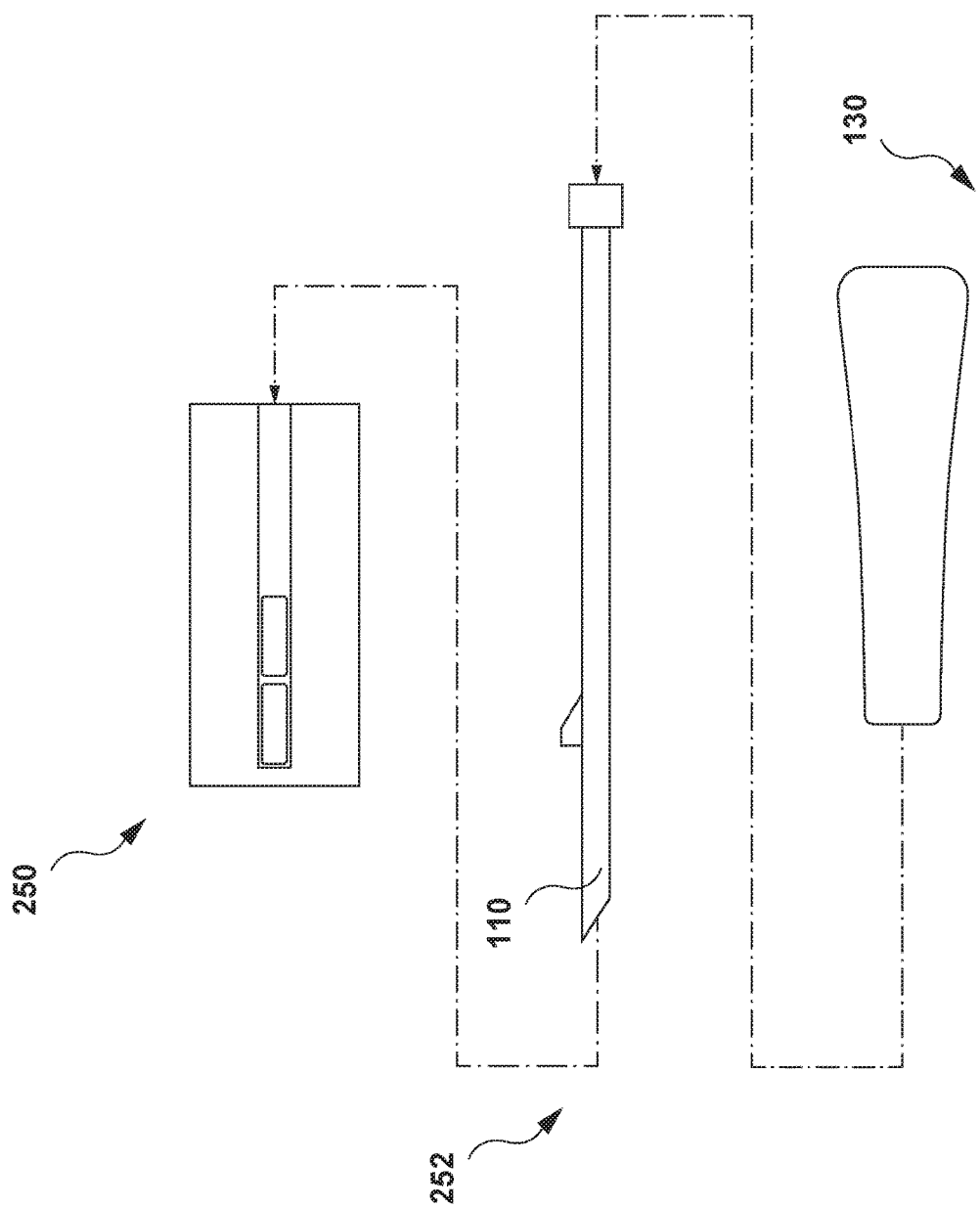

In still another example, as shown in FIG. 7F, a first loading device 250 is provided for holding the suture 50 and tabs 52. A second loading device 252 is provided that comprises a needle shaft of the needle 110. The needle 110 is inserted into the first loading device 250 to load the tabs 52 therein. The handle 130 may then be attached to the needle 110 to facilitate use thereof to deploy the tabs 52 from the suture passer 102 to enable treatment of a defect in tissue, such as a disc herniation.

Figure 8A:
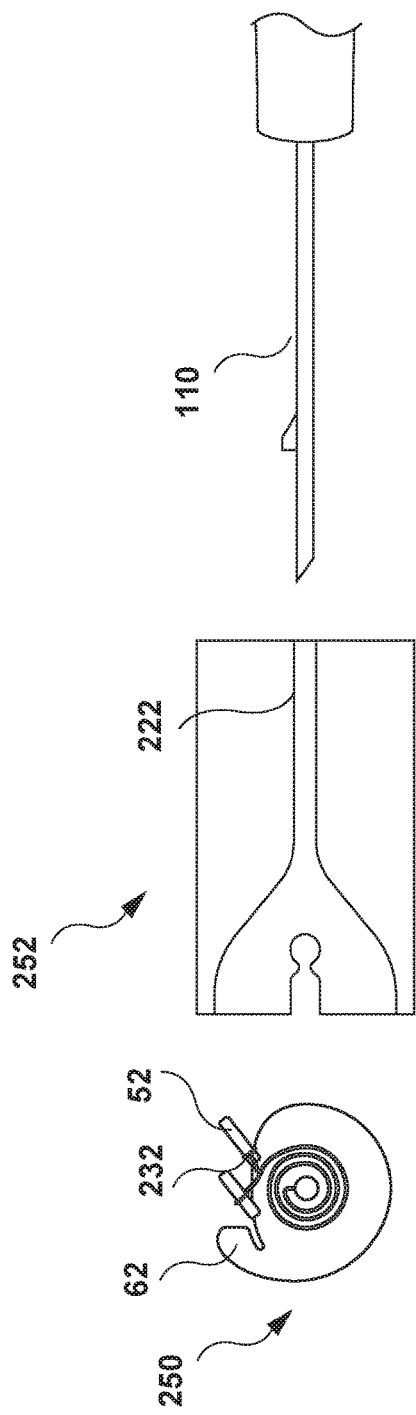
FIGS. 8A-8G are illustrations of loading devices in accordance with alternate embodiments of the present invention.
Figure 8B:
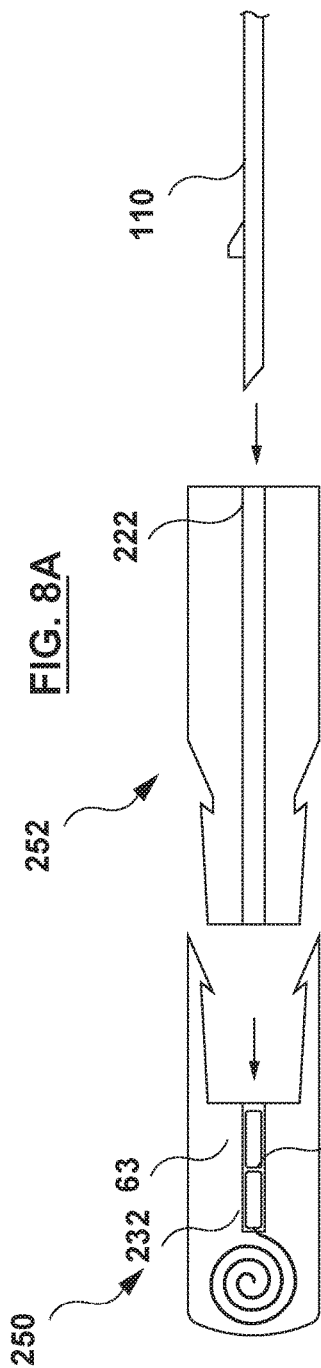
Figure 8C:
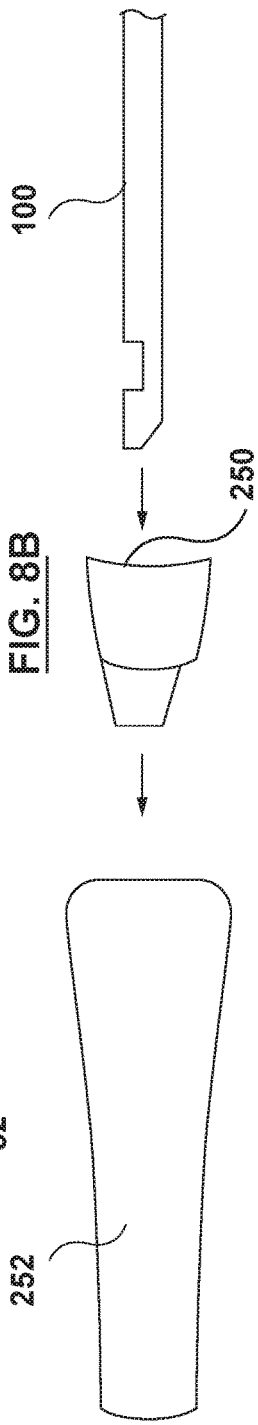

In another example, as shown in FIGS. 8A and 8B, a first loading device 250 is provided as a suture reel/spool 62 or a cartridge clip 63. The second loading device 252 functions as a loading mechanism and clips onto the first loading device 250. The suture passer 102 loads from the second loading device 252. In other words, the second loading device 252 functions as an interface between the two [the first loading device containing the tabs and the suture passer 102]. The first loading device 250 defines the tab holding passage 232 and holds the tabs 52 therein. The second loading device defines the delivery device receiving passage 222. As shown in FIG. 8B, the second loading device 252 additionally defines a loading device receiving passage 223 for receiving the first loading device 250 therein, and additionally defines an engagement feature 224 for co-operatively engaging with the first loading device 250. Alternatively, as shown in FIG. 8B, the first loading device 250 may comprise the loading device receiving passage 223. In another example [8C], the second loading device 252 comprises a cartridge defining a seat that defines a channel 232 for holding one or more ends of a suture, which in some examples may comprise one or more tabs 52, and the first loading component 250 may comprise a knot slider for holding a pre-tied knot thereon. The first and second loading devices 250, 252 define the delivery device receiving passage 222. The first and second loading components 250, 252 may assist with loading of the one or more ends of the suture [for example that may include tabs 52] and a pre-tied knot onto the suture passer 102. In one such example, one of the loading devices, such as the first loading device 250 may remain coupled to the suture passer 102 during use.

Figure 8D:
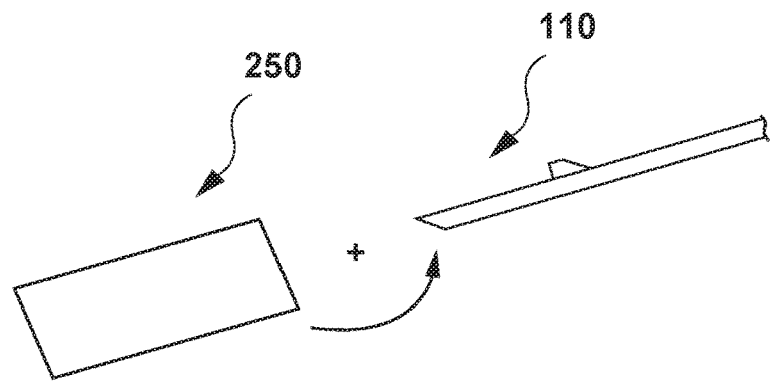
Figure 8E:
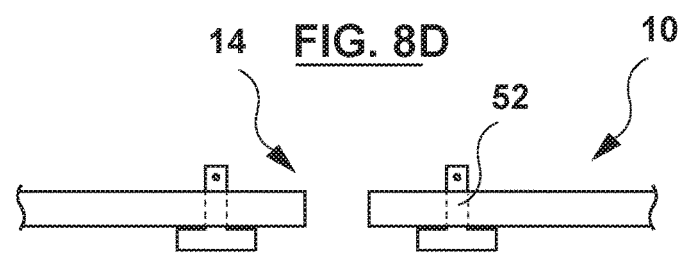
Figure 8F:
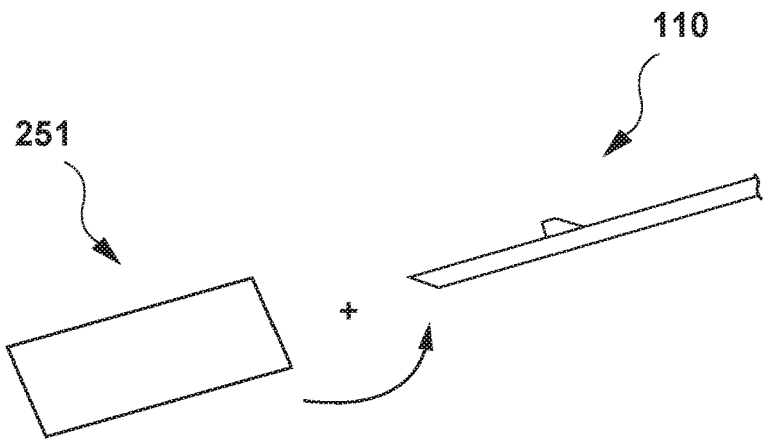
Figure 8G:
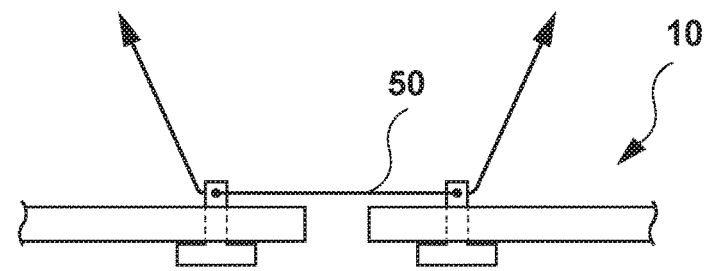

In an alternative embodiment of the present invention, a first loading device 250 may be provided to load the tabs 52 onto the suture passer 102, as shown in FIG. 8D, or directly into the tissue or tissue site 10 at the defect 14, as shown in FIG. 8E. If the tabs 52 are loaded into the suture passer 102, the suture passer 102 loads tabs 52 into the tissue. Once the tabs 52 are loaded into the tissue, the second loading device 252 loads suture 50 into the suture passer 102 [FIG. 8F]. The suture passer 102 passes suture through the tabs to create a stitch [FIG. 8G].

Figure 9B:
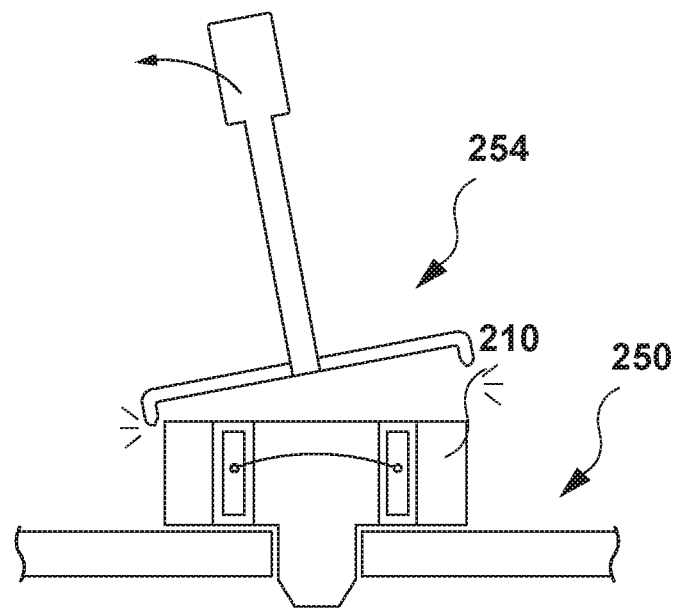

In another embodiment of the present invention, as shown in FIG. 9A, the first loading device 250 comprises a die card 60 that contains the suture tabs 52. The second loading device 252 defines a cartridge 200 where the tabs 52 are loaded/inserted onto the cartridge [for example in passages 232] using another device 300 such as tweezers using an indirect method. The tabs 52 are then loaded onto the suture passer 102 using a direct means from the cartridge 200 [such as by advancing needle 110 into the delivery device receiving passage 222].

Figure 9C:
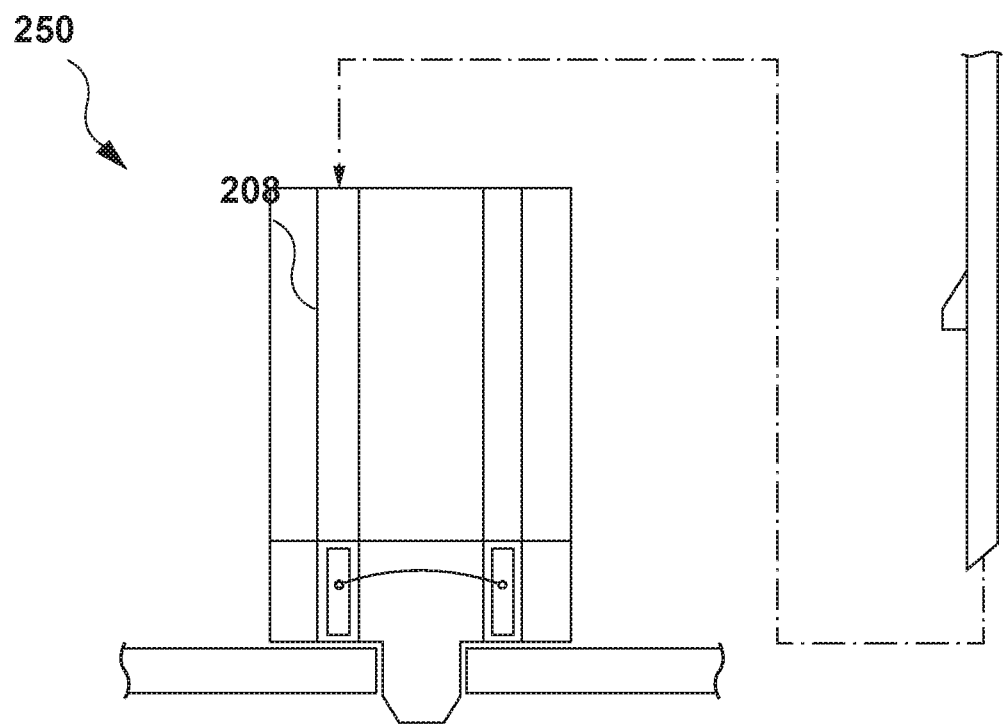

In one embodiment, the first loading device 250 comprises a cartridge attachment/suture plug 210 as shown in FIGS. 4F to 4P that additionally comprises a handle 254. The first loading device 250 is placed at the tissue 10 using the handle 254 [FIG. 9B]. The second loading device 252 comprises cartridge body 208. The second loading device 252 functions as the loading mechanism and is attached to the cartridge or first loading device 250. The suture passer 102 is then loaded through the second loading device 252 [FIG. 9C].

Figure 10A:
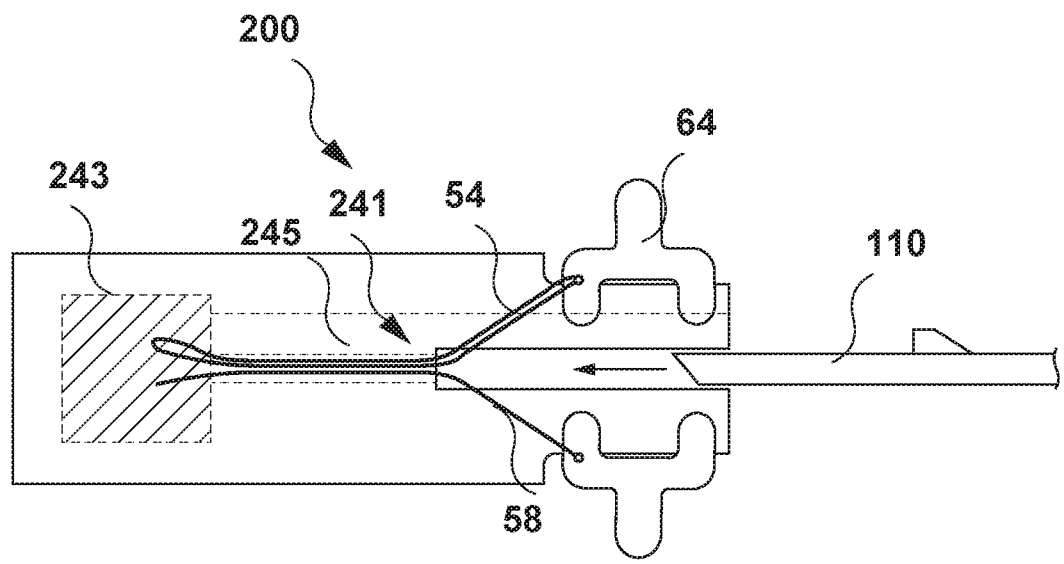

In some embodiments of the present invention, as shown in FIG. 10A, a cartridge 200 is provided that comprises a tether holding feature 241 and a tether loading feature/transferring feature or mechanism 243. The tether holding feature 241 comprises a tether holding passage 245 for holding the tether 54 therein. The cartridge 200 additionally comprises a suture holding feature 251 and a suture loading feature/transferring feature 253. In one example the suture holding feature 251 is the same as the tether holding feature 241, [and as such suture holding passage 255 is same as a tether holding passage 245]. Additionally, a holding/transferring feature 231/233 is provided. The tether 54 and suture such as the locker strand 58 are coupled to the cartridge 200 using the clips 64.

The method comprises inserting a needle 110 into the cartridge 200 and inserting the tabs 52 into the suture passer 102 using the tab holding/transferring feature 231/233. Idris The method additionally comprises disengaging the tether and suture clips 64 and attaching to the handle 130 of the suture passer 102. The shaft of the needle 110 is then removed and used to pass a stitch by deploying tabs 52 through tissue. A suture cutter 67 is provided to cut tether before removal of device from tissue site.

Figure 10B:
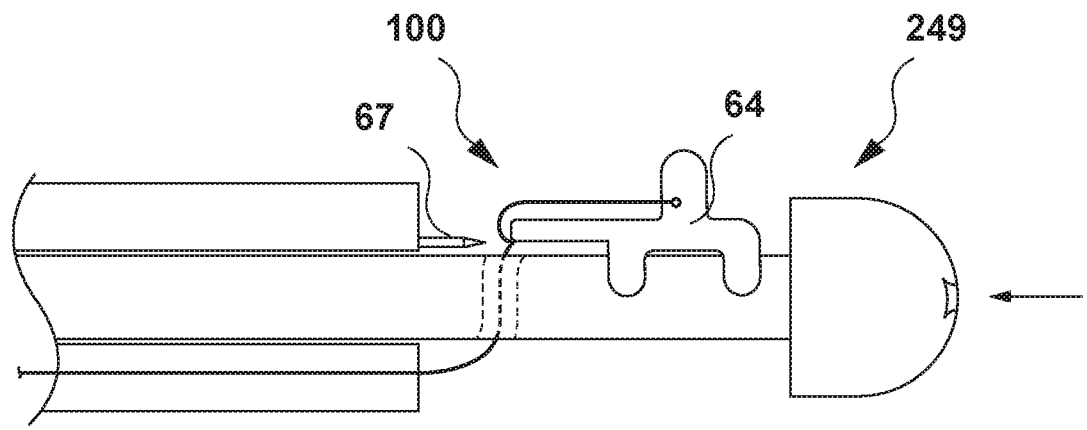

In one such example, as shown in FIG. 10B, an automated mechanism is provided where tether 54 is automatically cut as the actuator button is depressed, the tether is pressed against the blade of the suture cutter and cut.

In still another embodiment, the tether 54 attachment is locked onto the needle 110 by the cartridge 200 [for example via an elastic band 61], as shown in FIG. 10C. In one such example, the tether may be cut manually using a scalpel 500. Still alternatively, the tether may be snagged into the slot 118 [FIG. 10D]. Upon traveling of the stylet 120 at actuation of actuator 249 at second pass the tether 54 is cut by the sharp edge of the stylet 120 [FIG. 10E].

Figure 11A:
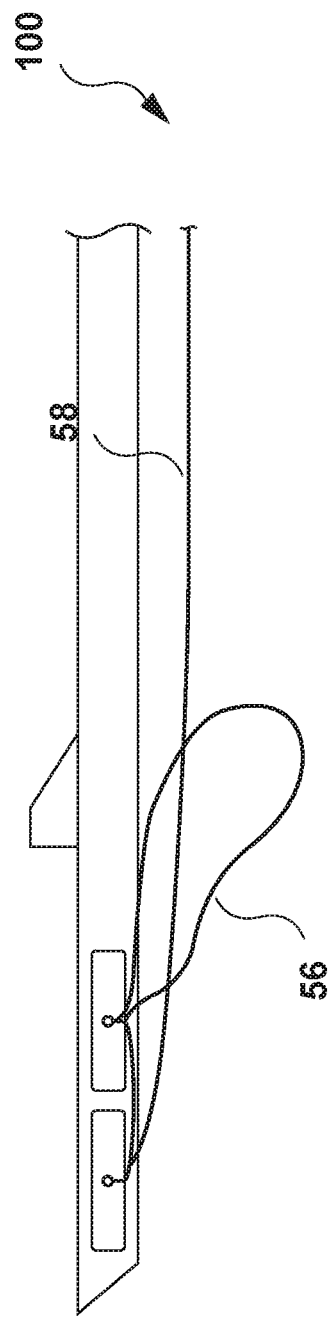
FIGS. 11A-11C are illustrations of loading devices in accordance with alternate embodiments of the present invention.
Figure 11B:
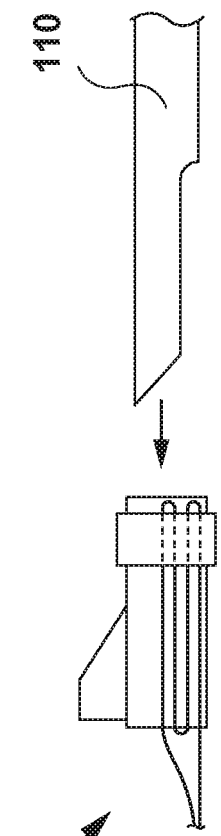
Figure 11C:
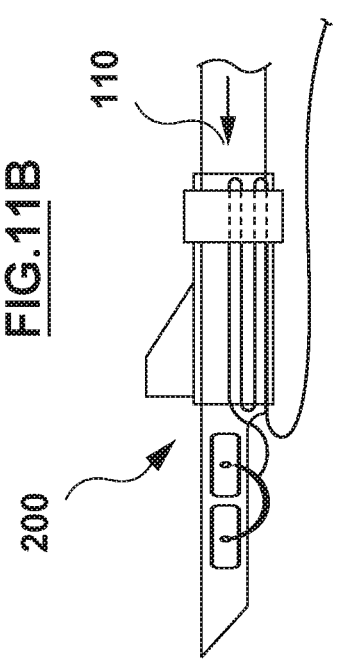

In another example, as shown in FIG. 11B and FIG. 11C, the cartridge 200 is provided for loading the device 100, where the cartridge 200 additionally comprises a suture holding feature 251 and a suture loading feature or transferring feature 253. This facilitates management of the suture 50 during loading and during use to prevent hindrance in visualization, and to minimize risk of snagging or tangling. The cartridge comprises the device stop or protrusion 125 is integrated with an affixing means 65 comprising a suture retention band to operate as part of the cartridge 200 that is loaded onto the suture passer 102 to form a part thereof.

In some embodiments of the present invention, one or more embodiments described in the present disclosure may be provided as a kit. For example in some such embodiments a kit is provided comprising a delivery device as provided hereinabove and a cartridge as provided herein above.

Thus, in one broad aspect, embodiments of the present invention provide a method of treating an intervertebral disc the method comprising: loading a closing device into a delivery device at the point of use, the closing device comprising tabs attached to a suture; and using the delivery device to close a defect of the intervertebral disc by means of the closing device.

In another broad aspect, embodiments of the present invention provide a cartridge for loading a closing device onto a delivery device at the point of use, the cartridge comprising: a tab holding feature for holding one or more tabs of the closing device; and a tab loading/transferring feature for loading tabs onto the delivery device.

As a feature of this broad aspect, the cartridge comprises a tether holding feature for holding a tether of the closing device; and a tether loading/transferring feature for loading the tether onto the delivery device.

As another feature of this broad aspect, the cartridge further comprising: a suture holding feature for holding a suture coupled to the one or more tabs, wherein each of the tabs is coupled to an end of the suture; and a suture loading/transferring feature for loading the suture onto the delivery device for securing the suture thereto.

As still another feature of this broad aspect, the cartridge further comprises a delivery device engagement/alignment feature for co-operatively engaging with the delivery device to enable transfer of the one or more tabs onto the delivery device.

As still another feature of this broad aspect, the cartridge comprises a tab holding feature comprises a seat for holding the one or more tabs therein; and the delivery device engagement feature comprises a delivery device receiving passage in communication with the seat for receiving a portion of the delivery device therein.

As another feature of this broad aspect, the delivery device engagement/alignment feature comprises a needle engagement/alignment feature for co-operatively engaging with the delivery device to enable transfer of the one or more tabs into a needle of the delivery device.

As another feature of this broad aspect, the tab holding feature comprises a tab holding passage defining a seat for holding the one or more tabs therein; and the needle engagement feature comprises a needle receiving passage in communication with the tab holding passage for receiving the needle therein.

As a further feature of this broad aspect, the seat defines a tab holding passage for holding the one or more tabs.

As a further feature of this broad aspect, the seat defines a projection for holding the one or more tabs thereon.

In one broad aspect, embodiments of the present invention provide methods and devices for facilitating loading of an implement such as a closing device onto a delivery device at the point of use. As a feature of this broad aspect, some embodiments of the present invention provide methods and devices for putting an implement such as a closing device onto the delivery device at the point of use to perform herniated disc repair.

In one broad aspect, embodiments of the present invention provide a method for loading an implement onto a delivery device at the point of use.

In a further broad aspect, embodiments of the present invention provide a loading device for loading an implement onto a delivery device.

In still a further broad aspect, embodiments of the present invention provide a loading device for loading an implement onto a delivery device, wherein the loading device may remain coupled to the delivery device for the remainder of the procedure.

In still a further broad aspect, embodiments of the present invention provide at least two loading devices for loading an implement onto a delivery device. As a feature of this broad aspect, the at least two loading devices are used substantially concurrently to load the implement onto the delivery device. As another feature of this broad aspect, the at least two loading devices are used sequentially to load the implement onto the delivery device. As still another feature of this broad aspect, the at least two loading devices comprise three or more loading devices for loading an implement onto the delivery device.

The embodiment(s) of the invention described above (are) intended to be exemplary only. The scope of the invention is therefore intended to be limited solely by the scope of the appended examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended examples. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method of treating an intervertebral disc, the method comprising:
    loading a closing device from a cartridge into a delivery device at a point of use, the closing device comprising at least two tabs coupled to a connecting element and the cartridge comprising a tab holding feature comprising a projection for holding the at least two tabs thereon; and
    substantially approximating a defect in the intervertebral disc using the closing device delivered by the delivery device.

2. The method of claim 1 wherein the cartridge further comprises a tab loading feature for loading tabs onto the delivery device to load the closing device onto a delivery device.

3. The method of claim 1, wherein the step of loading the closing device comprises pushing the closing device onto the delivery device.

4. The method of claim 2, wherein the step of loading the closing device comprises transferring the closing device directly onto the delivery device.

* * * * *